United States Patent [19]
Young, Sr. et al.

[11] Patent Number: 5,432,000
[45] Date of Patent: Jul. 11, 1995

[54] BINDER COATED DISCONTINUOUS FIBERS WITH ADHERED PARTICULATE MATERIALS

[75] Inventors: Richard H. Young, Sr., Federal Way; Amar N. Neogi, Seattle; Michael R. Hansen, Seattle; Kevin T. Hodgson, Seattle; Donald D. Halabisky, Tacoma; David G. Marsh, Federal Way; Christel Brunnenkant, Seattle; David W. Park, Puyallup; Paul G. Gaddis, Renton; William C. Johnston, Jr., Puyallup, all of Wash.

[73] Assignee: Weyerhaeuser Company, Tacoma, Wash.

[21] Appl. No.: 673,899

[22] Filed: Mar. 22, 1991

Related U.S. Application Data

[63] Continuation-in-part of Ser. No. 326,188, Mar. 20, 1989, Pat. No. 5,230,959, Ser. No. 326,181, Mar. 20, 1989, and Ser. No. 326,196, Mar. 20, 1989.

[51] Int. Cl.$^6$ .............................. D02G 3/00
[52] U.S. Cl. .................... 428/372; 428/357; 428/361; 428/373; 428/378; 428/393; 428/375
[58] Field of Search ............ 428/361, 372, 373, 374, 428/375, 389; 604/288, 368

[56] References Cited

U.S. PATENT DOCUMENTS

| | | | |
|---|---|---|---|
| 2,601,597 | 9/1946 | Daniel | 428/405 |
| 2,746,608 | 5/1956 | Briggs | 427/202 |
| 2,757,150 | 7/1956 | Heritage | 524/14 |
| 2,950,752 | 8/1960 | Watson et al. | 154/1 |
| 3,010,161 | 11/1961 | Duvall | 19/156 |
| 3,021,242 | 2/1962 | Touey | 427/202 |
| 3,081,207 | 3/1963 | Fox | 154/44 |
| 3,361,632 | 1/1968 | Gagliardi et al. | 117/143 A |
| 3,490,454 | 1/1970 | Goldfarb et al. | 128/283 |
| 3,494,992 | 2/1970 | Wiegand | 264/121 |
| 3,577,312 | 5/1971 | Videen et al. | 162/148 |
| 3,616,002 | 10/1971 | Paquette et al. | 156/180 |
| 3,671,296 | 6/1972 | Funakoshi et al. | 117/100 B |

(List continued on next page.)

FOREIGN PATENT DOCUMENTS

| | | |
|---|---|---|
| 0043040 | 1/1982 | European Pat. Off. . |
| 0084708 | 8/1983 | European Pat. Off. . |
| 0103214 | 3/1984 | European Pat. Off. . |
| 0160560 | 11/1985 | European Pat. Off. . |
| 0306202 | 8/1987 | European Pat. Off. . |
| 0341951 | 11/1988 | European Pat. Off. . |
| 0311344 | 4/1989 | European Pat. Off. . |
| 0327327 | 8/1989 | European Pat. Off. . |
| 0389015 | 9/1990 | European Pat. Off. . |
| 0392528 | 10/1990 | European Pat. Off. . |
| 1048013 | 6/1958 | Germany . |
| 2023659 | 11/1971 | Germany . |
| 90/01505 | 3/1990 | WIPO .............. B27K 3/00 |
| 90/01506 | 3/1990 | WIPO .............. B32B 5/16 |
| 90/01507 | 3/1990 | WIPO .............. B32B 5/16 |
| 90/01508 | 3/1990 | WIPO . |
| 90/01580 | 3/1990 | WIPO . |
| 90/01591 | 3/1990 | WIPO .............. B27K 3/00 |
| 90/11170 | 3/1990 | WIPO . |
| 90/11171 | 3/1990 | WIPO . |
| 90/11181 | 3/1990 | WIPO . |

OTHER PUBLICATIONS

PCT/US92/02424: PCT International Search Report mailed Sep. 9, 1992.

*Primary Examiner*—Patrick J. Ryan
*Assistant Examiner*—J. M. Gray
*Attorney, Agent, or Firm*—Klarquist Sparkman Campbell Leigh & Whinston

[57] ABSTRACT

A fiber product comprises dry discontinuous fibers having a starch binder on at least a portion of the fiber surfaces, at least about seventy percent of the starch binder coated fibers being unbonded to one another, solid particles are adhered to the fibers by the binder without the binder entirely coating the particles. The fibers may be air laid into a web or formed into an absorbent structure. Superabsorbent particles are a specific example of the particles which may be adhered to the fibers.

7 Claims, 14 Drawing Sheets

U.S. PATENT DOCUMENTS

| | | | |
|---|---|---|---|
| 3,672,945 | 6/1972 | Taylor | 427/214 |
| 3,673,021 | 6/1972 | Joa | 156/62.4 |
| 3,687,749 | 8/1972 | Reinhall | 156/62.4 |
| 3,734,471 | 5/1973 | Engels | 259/6 |
| 3,752,733 | 8/1973 | Graham et al. | 161/170 |
| 3,765,971 | 10/1973 | Fleissner | 156/62.4 |
| 3,775,210 | 11/1973 | Paquette et al. | 156/181 |
| 3,791,783 | 2/1974 | Damon et al. | 425/82 |
| 3,810,841 | 5/1974 | Richter | 252/91 |
| 3,836,412 | 9/1974 | Boustany et al. | 156/62.4 |
| 3,850,601 | 11/1974 | Stapleford et al. | 428/220 |
| 3,868,955 | 3/1975 | Steiger et al. | 128/296 |
| 3,901,236 | 8/1975 | Assarsson et al. | 128/28 |
| 3,914,498 | 10/1975 | Videen | 428/290 |
| 3,916,825 | 11/1975 | Schnitzler et al. | 118/303 |
| 3,942,729 | 5/1976 | Fredriksson | 241/38 |
| 3,967,005 | 6/1976 | Cattaneo | 407/202 |
| 3,974,307 | 8/1976 | Bowen | 427/212 |
| 3,991,225 | 11/1976 | Blouin | 427/3 |
| 3,992,558 | 11/1976 | Smith-Johannsen et al. | 427/213 |
| 4,006,706 | 2/1977 | Lodige et al. | 118/303 |
| 4,006,887 | 2/1977 | Engels | 259/9 |
| 4,009,313 | 2/1977 | Crawford et al. | 428/290 |
| 4,010,308 | 3/1977 | Wiczer | 428/375 |
| 4,015,830 | 4/1977 | Lodige et al. | 259/25 |
| 4,039,645 | 8/1977 | Coyle | 264/118 |
| 4,100,328 | 7/1978 | Gallagher | 428/407 |
| 4,111,730 | 9/1978 | Balatinecz | 156/622 |
| 4,129,132 | 12/1978 | Butterworth | |
| 4,143,975 | 5/1979 | Lodige et al. | 366/147 |
| 4,153,488 | 5/1979 | Wiegand | 156/62.2 |
| 4,160,059 | 7/1979 | Samejima | 428/288 |
| 4,168,919 | 9/1979 | Rosen et al. | 366/173 |
| 4,183,997 | 1/1980 | Stofko | 428/326 |
| 4,187,342 | 2/1980 | Holst et al. | 428/283 |
| 4,188,130 | 2/1980 | Engels | 366/228 |
| 4,191,224 | 3/1980 | Bontrager et al. | 141/100 |
| 4,193,700 | 3/1980 | Wirz | 366/156 |
| 4,241,133 | 12/1980 | Lund et al. | 428/326 |
| 4,241,692 | 12/1980 | Van Hijfte et al. | 118/303 |
| 4,242,241 | 12/1980 | Rosen et al. | 260/17.2 |
| 4,248,685 | 2/1981 | Beede et al. | 204/159.22 |
| 4,252,844 | 2/1981 | Nesgood et al. | 427/213 |
| 4,261,943 | 4/1981 | McCorsley, III | 264/136 |
| 4,297,253 | 10/1981 | Sorbier | 260/17.3 |
| 4,302,488 | 11/1981 | Lowi, Jr. | 427/212 |
| 4,320,166 | 3/1982 | Endo et al. | 428/283 |
| 4,320,715 | 3/1982 | Maloney et al. | 118/303 |
| 4,323,625 | 4/1982 | Coran | 428/361 |
| 4,337,722 | 7/1982 | Debayeaux et al. | 118/303 |
| 4,354,450 | 10/1982 | Nagahama et al. | 118/303 |
| 4,360,545 | 11/1982 | Maloney et al. | 427/212 |
| 4,364,992 | 12/1982 | Ito et al. | 428/283 |
| 4,370,945 | 2/1983 | Beckschulte et al. | 118/303 |
| 4,379,194 | 4/1983 | Clarke et al. | 428/203 |
| 4,379,196 | 4/1983 | Hunt | 428/196 |
| 4,392,908 | 7/1983 | Dehnel | 427/194 |
| 4,404,250 | 9/1983 | Clarke et al. | 428/220 |
| 4,407,771 | 10/1983 | Betzner et al. | 264/115 |
| 4,408,996 | 10/1983 | Baldwin | 8/490 |
| 4,418,676 | 12/1983 | Paquette et al. | 156/181 |
| 4,424,247 | 1/1984 | Erickson | 428/138 |
| 4,425,126 | 1/1984 | Butterworth | 604/366 |
| 4,426,417 | 1/1984 | Meitner et al. | 428/195 |
| 4,428,843 | 1/1984 | Cowan et al. | 252/85 |
| 4,429,001 | 1/1984 | Kolpin et al. | 428/283 |
| 4,430,003 | 2/1984 | Beattie et al. | 366/173 |
| 4,435,234 | 3/1984 | Hunt | 156/62.4 |
| 4,439,489 | 3/1984 | Johnson et al. | 428/404 |
| 4,444,267 | 4/1984 | Coran | 428/288 |
| 4,444,810 | 4/1984 | Huttlin | 427/212 |
| 4,457,978 | 7/1984 | Wawzonek | 524/14 |
| 4,465,017 | 8/1984 | Simmons | 118/418 |
| 4,468,264 | 8/1984 | Clarke et al. | 156/62.4 |
| 4,469,746 | 9/1984 | Weisman et al. | 428/289 |
| 4,478,986 | 10/1984 | Barnes et al. | 427/421 |
| 4,486,501 | 12/1984 | Holbek | 428/375 |
| 4,487,365 | 12/1984 | Sperber | 239/8 |
| 4,492,729 | 1/1985 | Bannerman et al. | 428/283 |
| 4,500,384 | 2/1985 | Tomioka et al. | 156/290 |
| 4,510,184 | 4/1985 | Winkler et al. | 427/212 |
| 4,514,255 | 4/1985 | Maxwell et al. | 162/9 |
| 4,516,524 | 5/1985 | McClellan et al. | 118/683 |
| 4,547,403 | 10/1985 | Smith | 427/196 |
| 4,559,050 | 12/1985 | Iskra | 604/368 |
| 4,572,100 | 2/1986 | Schluter | 118/303 |
| 4,572,845 | 2/1986 | Christen | 427/212 |
| 4,584,357 | 4/1986 | Harding | 525/54 |
| 4,592,302 | 6/1986 | Motoyama et al. | 118/303 |
| 4,596,737 | 6/1986 | Werbowy et al. | 428/228 |
| 4,600,462 | 7/1986 | Watt | 156/278 |
| 4,610,678 | 9/1986 | Weisman et al. | 604/368 |
| 4,615,689 | 10/1986 | Murray et al. | 493/51 |
| 4,647,324 | 3/1987 | Mtangi et al. | 156/62.2 |
| 4,648,920 | 3/1987 | Sperber | 156/62.2 |
| 4,656,056 | 4/1987 | Leuenberger | 427/213 |
| 4,664,969 | 5/1987 | Rossi et al. | 428/284 |
| 4,673,402 | 6/1987 | Weisman et al. | 604/368 |
| 4,673,594 | 6/1987 | Smith | 427/196 |
| 4,676,784 | 6/1987 | Erdman et al. | 604/368 |
| 4,689,249 | 8/1987 | Thygesen | 427/180 |
| 4,722,860 | 2/1988 | Doljack et al. | 428/260 |
| 4,746,547 | 5/1988 | Brown et al. | 427/213 |
| 4,749,595 | 6/1988 | Honda | 427/213 |
| 4,758,466 | 7/1988 | Dabi et al. | 428/283 |
| 4,772,443 | 9/1988 | Thornton et al. | 264/119 |
| 4,788,080 | 11/1988 | Hojo et al. | 427/204 |
| 4,806,598 | 2/1989 | Morman | 525/63 |
| 4,818,587 | 4/1989 | Ejima et al. | 428/198 |
| 4,818,599 | 4/1989 | Marcus | 428/288 |
| 4,818,613 | 4/1989 | Ohtani et al. | 428/396 |
| 4,872,870 | 10/1989 | Jackson | 604/366 |
| 4,937,100 | 6/1990 | Lanters et al. | 427/212 |
| 4,943,477 | 7/1990 | Kanamura et al. | 428/286 |
| 4,979,318 | 1/1991 | Brooker et al. | 428/283 |
| 4,983,452 | 1/1991 | Daimon et al. | 428/287 |

5,432,000

BINDER COATED DISCONTINUOUS FIBERS WITH ADHERED PARTICULATE MATERIALS

CROSS REFERENCE TO RELATED APPLICATIONS

This is a continuation-in-part application of U.S. patent application Ser. Nos. 07/326,188, filed Mar. 20, 1989, now U.S. Pat. No. 5,230,959, entitled "A Coated Fiber Product With Super Absorbent Particles"; 07/326,181, filed Mar. 20, 1989, entitled "A Natural Fiber Product Coated With A Thermoset Binder Material"; and 07/326,196, filed Mar. 20, 1989, entitled "A Natural Fiber Product With A Thermoplastic Binder Material".

BACKGROUND OF THE INVENTION

The present invention relates to discontinuous fibers with a binder material coating which adheres solid particulate material to the fibers and to absorbent structures of such materials.

A number of techniques for applying binders to webs of fibers are known. For example, U.S. Pat. No. 4,600,462 of Watt describes a process in which an adhesive binder is sprayed onto one or both surfaces of an air laid cellulose fiber web. Submersion of the web in the adhesive binder is another method disclosed in this patent of applying the binder. Individual binder coated fibers for mixing with other fibers are not produced by this process. A hydrophile solution is also applied to the web. As another example, U.S. Pat. Nos. 4,425,126 and 4,129,132 of Butterworth, et al. describe a fibrous material formed by combining thermoplastic fibers and wood pulp, heat fusing the combined fibers, and thereafter depositing a binder on the heat fused web. Because the fibers are heat fused prior to adding the binder, individual binder coated fibers for mixing with other fibers are not produced by this process.

U.S. Pat. No. 4,584,357 of Harding discloses a latex treated cationic cellulose product and method for its manufacture. In the Harding approach, cationized cellulose is treated in an aqueous suspension with an anionic polymer emulsion of from 0.1 to 30 percent on a dry weight basis. The patent mentions that the resulting resin treated products can be prepared in sheet form, as loose fibers or in another form. The approach of the Harding patent is limited to cationic fibers. Also, the fiber coating applied as described in the Harding patent had a tendency to flake off or separate from the fibers. Moreover, because the Harding approach uses a wet process, the lumen of the cellulose fibers is penetrated by the polymer emulsion. Since the binder on the surface of the fibers contributes principally to the desired characteristics of the fiber, any polymer that penetrates the lumen of the fiber adds little to these desired characteristics.

U.S. Pat. No. 4,469,746 of Weisman, et al. discloses fibrous webs comprised of fibers coated with a continuous film of silica. The fibers are understood to be dispersed in a charged silica aquasol to accomplish the coating. Because silica is an inorganic material, the silica does not contribute to subsequent bonding of fibers. In addition, because Weisman, et al. discloses a wet process, the silica will tend to penetrate the lumen of cellulose fibers in the event such fibers are being treated in accordance with this patent.

U.S. patent application Ser. No. 067,669, filed Jun. 26, 1987, and entitled "Treated Wood Fiber Having Hydrophobic and Oleophilic Properties" by Jewell, et al., mentions an approach of treating fiberized wood with surfactant material to penetrate the surface of the wood fibers. In this approach, fiberized wood at the outlet of a first fiberizing machine passes through an orifice into a blow line. At the outlet of the fiberizing machine, liquid surfactant is injected into the line. At the point of addition of the surfactant, the fiber is still wet as it has been carried by steam through the fiberizing machine. Surfactants are not suitable for use in subsequent bonding of the fibers. The Jewell, et al. patent application also describes a process in which fibers are treated with a copolymer latex, such as a combination of a paraffin wax emulsion and a styrene butadiene copolymer latex. The patent describes a suitable treating process as involving the blending of the aqueous latex emulsion with wood fiber in a typical mechanical wood fiber blender. This approach tends to produce fibers which are bound together by the latex.

U.S. Pat. No. 2,757,150 of Heritage mentions a fiber treatment approach in which fibers are carried by steam under pressure and in which a thermoset resin is introduced into the fiber stream. Other materials (i.e. rosin and wax) are mentioned as being simultaneously introduced into the fiber stream. The patent indicates that such materials penetrate the surface of the fibers. This patent mentions the individualization of these treated fibers. A relatively low concentration of the thermoset resin (i.e. two percent by weight phenol formaldehyde) is specifically described in this patent. At such low concentrations, the resin is in discontinuous random non-interconnected areas (blobs or globules) on the fibers. These treated fibers are typically used in hardboard. In current hardboard resin products produced using the approach of the Heritage patent and known to the inventors, a phenolic resin concentration of from a maximum of five to six percent by weight is used. Even at these concentrations, the resin forms random non-interconnected globules on the fibers. As a result, the uncoated resin free areas of the fibers lack the capacity to bond in comparison to the areas of the fibers covered by the resin. In addition, the untreated surface areas of the fibers may lack desired characteristics of the resin covered areas of the fibers. For example, these uncoated areas may cause the fibers to be more water absorbent than if the entire fiber was coated.

U.S. Pat. No. 4,006,887 of Engels describes a process for treating wood fibers in which the fibers are supported as an annular loose fluidized bed in a mixer which delivers glue by way of shaft mounted mixing rods to the fibers. The patent mentions that radial air vortices are established with the mixer inlet and outlet funnels being connected to an air transport pipe. The patent describes the resulting product as homogenous lump free uniformly coated wood fibers. The patent mentions that the coating of fibers is useful in the manufacture of wood fiber panels. The glue used in the Engels patent and the percentage of the glue that is used is not discussed.

The background portion of the Engels patent describes German Auslegeschrift 1,048,013 as disclosing an impeller or agitator mixer for the coating of wood chips with dusty components. Glue is described as being sprayed through nozzles into a mixing container. An air stream is described as being blown axially through the mixing container in order to reduce the residence time of dusty chip particles to reduce excessive coating of such dusty particles. Also, German Offenlegunge 1,632,450 is mentioned by Engels as disclosing wood chips agitated in an air stream in a mixing tube in which glue spray nozzles are mounted.

Heretofore, synthetic bicomponent fibers have been formed by extruding two materials in air in side-by-side strands which are connected together along their length. Such bicomponent fibers have also been formed with one material being extruded as a concentric sheath surrounding the other material. These extruded strands are then chopped or broken into discontinuous fibers. Although synthetic bicomponent fibers provide good structural efficiency, they are very expensive in comparison to natural fibers, and, therefore, their use is limited.

U.S. Pat. No. 4,261,943 of McCorsley, III describes the extrusion of filaments and the application of a solution of a nonsolvent liquid to the filaments. In this application process;, the filaments are passed through a chamber having a nonsolvent vapor laden atmosphere, i.e. a fog of minute particles of nonsolvent. Spraying of the nonsolvent liquid onto the filaments is also mentioned. The approach of the McCorsley, III patent is not understood to apply to discontinuous fibers.

U.S. Pat. No. 4,010,308 of Wiczer describes foamed porous coated fibers. Fibers, described as organic or inorganic fibers of any character, are described as being coated with a foamable plastic material. Thermoplastic and thermosetting coatings are mentioned. In several examples, the coated fibers are made by passing continuous extruded filaments through a first bath of a ten percent polystyrene solution on toluene, evaporating the solvent, and passing the polystyrene coated fiber through a second bath containing a blowing agent, such as liquid n-pentane. The treated filaments are then heated to foam the coating. Rolls are used to rub solid particles into the porous surface of the foam coating. Fireproofing agents, lubricants such as graphite, pigments, and insecticides are among the examples of solid materials mentioned as suitable for rubbing into the coating. In another example, short lengths of cotton linters are described as being wet with a ten percent solution of a copolymer of polystyrene and acrylonitrile in about equal proportions dissolved in benzene. The solvent is evaporated in an air stream and the resulting coated cotton fiber is dipped in mixed pentanes. The product is then stirred in boiling water to cause foaming. Following foaming, the product is centrifugally dried and again dried in an air stream. The fiber is then mixed with a dry powder to fill the pores in the foamed coating with the powder. The placement of this fiber product in a container and heating the product to cause the adherence of the fiber surface contact points is also mentioned. The Wiczer patent appears to use a solution dipping approach as a means of applying the coating to the fibers.

U.S. Pat. No. 4,160,059 of Samejima describes a process in which a natural cellulose fiber (such as wood pulp fiber) is shredded and blended in air with a heat-fusible fiber. The blend is fed to a disintegrator to form supporting fibers to which an absorptive material is added. Heated air is applied to the resulting web to heat the web to a temperature above the melting point of the heat-fusible fiber to form bonds between the supporting fibers and absorptive material by heat fusion. Activated carbon black, Japanese acid clay, active alumina, and diatomaceous earth are mentioned as representative absorptive materials. Other powders, including super absorbents, are also mentioned as being bonded in place in this manner. The background portion of this particular patent also mentions a process in which wood pulp is disintegrated by a dry process, blended with active carbon black, and the blend spread on a wire screen. A binding material such as latex, starch and the like can also be sprayed on both surfaces of the web. With this latter approach, the active surface of the absorptive material is covered with a thin film of the binding material. Thus, under the Samejima approach, heat fusion is used to bind the particles to the fibers. As a result, a bound fiber web, as opposed to individualized fibers, is formed with the particles heat fused to the fibers. In U.S. Pat. No. 4,429,001 of Kolpin et al., melt-blown fibers are prepared by extruding liquid fiber-forming materials into a high-velocity gaseous stream. The stream of fibers is collected on a screen disposed in the stream with the fibers being collected as an entangled coherent mass. Absorbent particles are introduced into the stream of fibers at the point where the fibers are solidified sufficiently that the fibers will form only a point contact with the particles. The patent mentions that the particles can also be mixed with the fibers under conditions that will produce an area of contact with the particles. The introduction of other fibers besides melt-blown fibers into the resulting sheet product is also mentioned. The patent mentions that surfactants in powder form can be mixed with the sorbent particles used in forming the web or surfactants in liquid form can be sprayed onto the web after it is formed.

Finally, U.S. Pat. No. 4,392,908 of Dehnel describes a process for forming a thermoplastic adhesive resin on a surface of water soluble particles. The coated particles in a dry state are heated and pressed to bond them to a dry substrate (i.e. cellulose fluff). Mixing of absorbent particles with an aqueous latex, spraying resin onto the particles, and mixing the particles in a slurry are mentioned as approaches for coating the particles. Milling of the particles after coating with thermoplastic is mentioned as usually being necessary to produce free flowing particles. Thus, the Dehnel patent illustrates another approach for heat fusing particles to fibers.

Although prior art approaches are known, a need exists for improved discontinuous fibers with a binder material and with adhered particles.

SUMMARY OF THE INVENTION

In accordance with the present invention, bulk treated fibers are produced, a substantial majority of which have a substantial majority of their surface area continuously coated with a binder. Particles may also be adhered to the fibers by the binder. Most preferably, a substantial majority of the fibers, and more typically virtually all of the fibers, have a substantially continuous coating of a binder material. At least a substantial majority of the bulk treated fibers are unbonded so that they may be readily blended with other fibers and/or processed into products (such as by air laying techniques). By using a heat curable material as the binder, the fibers may be subsequently heated to cure the binder and fuse them together. The fibers may also be combined with other nontreated fibers and heat fused to provide an absorbent or other structure, with a bonded web being one specific example.

In accordance with the present invention, the fibers may have substantial amounts of binder material, yet still comprise individualized substantially continuously coated fibers. It has been found that the binder material must be included in an amount of at least about seven percent of the combined dry weight of the binder material and fibers in order to produce a substantially continuous binder coating on the fibers. With a substantially continuous coating, little or no surface area of the fibers is exposed and the desired characteristics added to the fibers by the binder material are not nullified or significantly altered by uncoated areas of the fiber. With a binder level of at least about ten percent of the combined dry weight of the binder material and fibers, the coated fibers are capable of bonding relatively strongly to one another when heat fused. In addition, fibers with binder levels of thirty percent to fifty percent and higher, such as above ninety percent and with no maximum limit yet being determined, are included in the invention, while still resulting in a product comprised of substantially unbonded individualized fibers. Also, high binder levels are preferably used to maximize the bonding and to adhere solid particulate materials to the fibers. For some particles, however, lower binder content may be used to reduce the possibility of the binder coating the particles and interfering with their functionalities.

The solid particulate material is adhered to the fibers by the binder material. Although not limited to specific materials, the particulate materials may comprise at least one material selected from the group comprising a pigment material, a super absorbent material, an electrically conductive material, a fertilizer, an insecticide, and a fire retardant material. Other examples of particles and particle categories are set forth in the specification below.

The coated fibers may also be stuck to super absorbent particles by the binder, therefore, the particles are substantially prevented from migrating or escaping from the fibers. Also, as explained below, the particles and fibers adhere without heat fusing any binder to accomplish this result. A substantial majority of the resulting binder coated fibers are typically adhered to the same super absorbent particle (SAP) if relatively large SAP particles are used (e.g. the SAP diameter being larger than the fiber diameter). By using an organic polymeric material as the liquid binder, and in particular a heat bondable liquid binder material, the fibers with the super absorbent particles may be subsequently heated to fuse them together. The fibers may also be combined with other nontreated fibers and heat fused to provide a bonded absorbent structure.

The particulate material is typically applied to the fibers while the liquid binder material on the fibers is still at least partially wet. As the liquid binder material dries, the super absorbent particulate material is adhered to the fibers.

In accordance with the invention, more than one binder material may be applied to the fibers, such as a thermoset binder material followed by a thermoplastic binder material, with the solid particulate material being adhered to the fibers by the binder. Again, substantially individualized fibers containing these plural binder materials can be produced.

Although not as beneficial for many applications, such as when the properties of individual fibers are desired, in addition to individual cellulose fibers, the fiber product may comprise cellulose fiber bundles. A fiber bundle is an interconnected group of two or more fibers that are not separated during processing. Fiber bundles, like individual fibers are much longer than wide. For example, when mechanically fiberized wood is produced, some individual fibers result along with fiber bundles of fibers that are not separated during the mechanical fiberization process.

It is accordingly one object of the present invention to provide improved discontinuous fibers coated with a binder material and to which particles are adhered by the binder material.

Another object of the present invention is to provide substantially individualized discontinuous binder coated fibers, with particulate materials adhered thereto, for use in the manufacture of absorbent structures, with or without additional untreated fibers being added.

These and other objects, features and advantages of the present invention will be apparent with reference to the following detailed description and drawings.

DETAILED DESCRIPTION OF THE PREFERRED EMBODIMENTS

Figure 1:
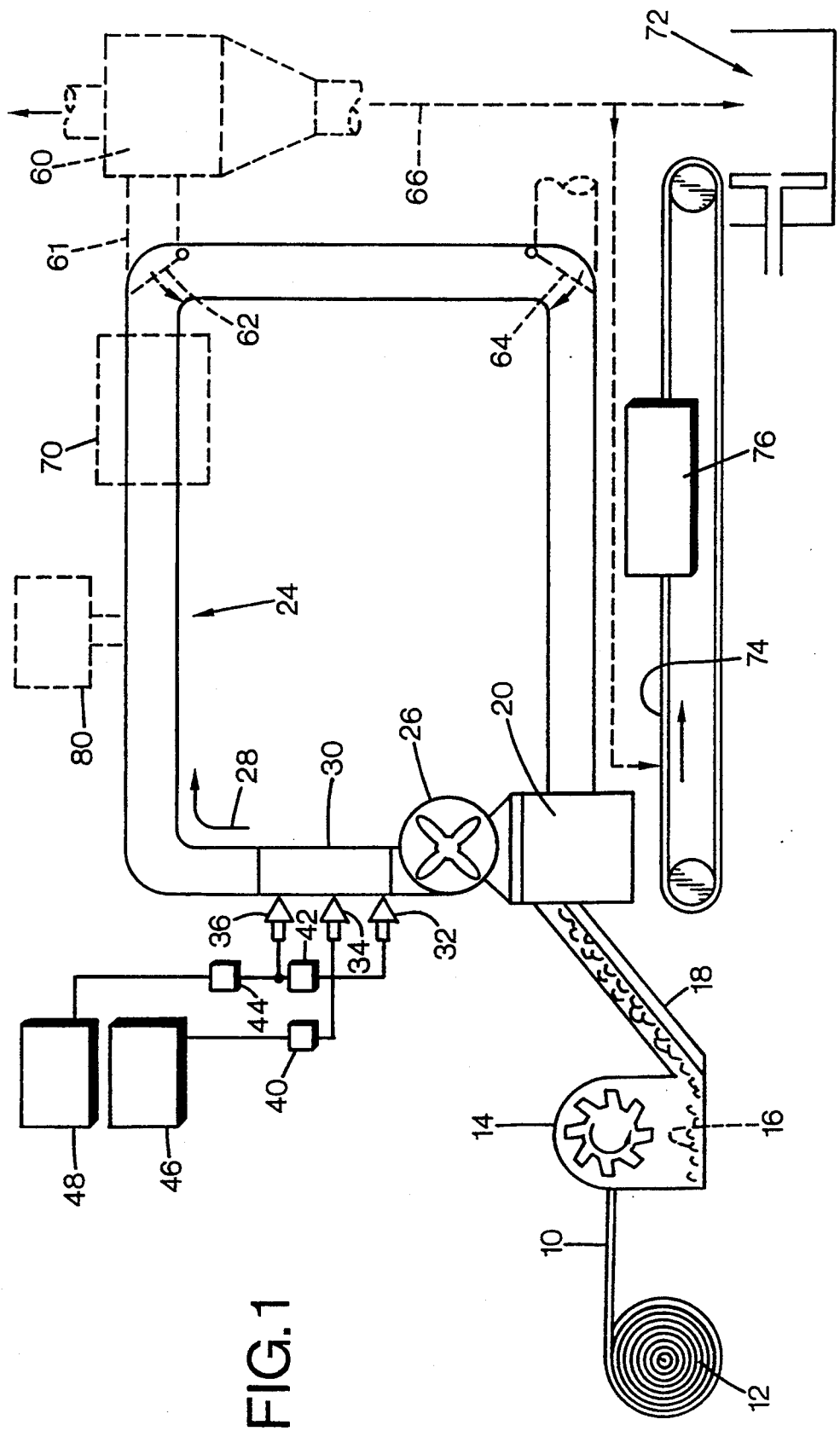
FIG. 1 is a schematic illustration of one form of apparatus in which discontinuous fibers of the present invention can be obtained.

The present invention is applicable to treated discontinuous synthetic and natural fibers. The term natural fibers refers to fibers which are naturally occurring, as opposed to synthetic fibers. Non-cellulosic natural fibers are included, with chopped silk fibers and wool being specific examples. In addition, the term natural fibers includes cellulosic fibers such as wood pulp, bagasse, hemp, jute, rice, wheat, bamboo, corn, sisal, cotton, flax, kenaf, and the like and mixtures thereof. The term discontinuous fibers refers to fibers of a relatively short length in comparison to continuous fibers treated during an extrusion process used to produce such fibers. The term discontinuous fibers also includes fiber bundles. The term individual fibers refers to fibers that are comprised substantially of individual separated fibers with at most only a small amount of fiber bundles. Chopped or broken synthetic fibers also fall into the category of discontinuous fibers. Although not limited to any particular type of fiber, the synthetic fibers commonly are of polyethylene, polypropylene, acrylic, polyester, polyaramid (e.g. KEVLAR TM polyaramid fibers), rayon and nylon. Discontinuous fibers of inorganic and organic materials, including cellulosic fibers, such as cellulose acetate, cellulose triacetate, etc., are also included. The natural fibers may likewise be of a wide variety of materials, such as mentioned previously. The fibers may be subjected to fibrillation, for example by mechanical or ultrasonic means to break the fibers into fibers of smaller cross sectional dimension and to disperse clumps or bundles of fiber prior to treatment.

Wood pulp fibers can be obtained from well-known chemical processes such as the Kraft and sulfite processes. Suitable starting materials for these processes include hardwood and softwood species, such as alder, pine, douglas fir, spruce and hemlock. Wood pulp fibers can also be obtained from mechanical processes, such as ground wood, refiner mechanical, thermomechanical, chemi-mechanical, and chemi-thermomechanical pulp processes. However, to the extent such processes produce fiber bundles as opposed to individually separated fibers or individual fibers, they are less preferred. However, treating fiber bundles is within the scope of the present invention. Recycled or secondary wood pulp fibers and bleached and unbleached wood pulp fibers can also be used. Details of the production of wood pulp fibers are well-known to those skilled in the art. These fibers are commercially available from a number of companies, including Weyerhaeuser Company, the assignee of the present patent application. Wood pulp fibers typically have an irregular or rough surface and, for this reason, are particularly difficult to coat on a substantially continuous basis.

For purposes of convenience, and not to be construed as a limitation, the following description proceeds with reference to the treatment of individual chemical wood pulp fibers. The treatment of individual fibers of other types and obtained by other methods, as well as the treatment of fiber bundles, can be accomplished in the same manner.

When relatively dry wood pulp fibers are being treated, that is fibers with less than about ten to twelve percent by weight moisture content, the lumen of such fibers is substantially collapsed. As a result, when binder materials, in particular latex binder materials, are applied to these relatively dry wood pulp fibers, penetration of the binder into the lumen is minimized. In comparison, relatively wet fibers tend to have open lumen through which binder materials can flow into the fiber in the event the fiber is immersed in the binder. Any binder that penetrates the lumen contributes less to the desired characteristics of the treated fiber than the binder which is present on the surface of the fiber. Therefore, when relatively dry wood pulp fibers are treated, less binder material is required to obtain the same effect than in the case where the fibers are relatively wet and the binder penetrates the lumen.

The fibers may be pretreated prior to the application of a binder to the fibers as explained below. This pretreatment may include physical treatment, such as subjecting the fibers to steam or chemical treatment, such as cross-linking the fibers. Although not to be construed as a limitation, examples of pretreating fibers include the application of fire retardants to the fibers, such as by spraying the fibers with fire retardant chemicals. Specific fire retardant chemicals include, by way of example, sodium borate/boric acid, urea, urea/phosphates, etc. In addition, the fibers may be pretreated with surfactants or other liquids, such as water or solvents, which modify the surface of the fibers. Sizing of fibers with sizing agents, such as starch, polymers and alkyl ketene dimer are yet other examples of possible fiber pretreatment. The fibers may also be pretreated in a way which increases their wettability. For example, natural fibers may be pretreated with a liquid sodium silicate, as by spraying the fibers with this material, for pretreatment purposes. Wettability of the surface of fibers is also improved by subjecting the fibers to a corona discharge pretreatment in which electrical current is discharged through the fibers in a conventional manner. In the case of both synthetic fibers and wood pulp fibers, corona discharge pretreatment results in oxygen functionality on the surface of the fibers, making them more wettable. The fibers may also be pretreated with conventional cross-linking materials and may be twisted or crimped, as desired. Pretreating cellulose fibers with chemicals which result in lignin or cellulose rich fiber surfaces may also be performed in a conventional manner. Also, pretreatment with materials such as silane enhances the adhesion between fibers and polymers or other substances. Bleaching processes, such as chlorine or ozone/oxygen bleaching may also be used in pretreating the fibers. In addition, the fibers may be pretreated, as by slurrying the fibers in baths containing antimicrobial solutions (such as solutions of antimicrobial particles as set forth below), fertilizers and pesticides, and/or fragrances and flavors, for release over time during the life of the fibers. Fibers pretreated with other chemicals, such as thermoplastic and thermoset resins may also be used. Combinations of pretreatments may also be employed with the resulting pretreated fibers then being subjected to the application of the binder coating as explained below.

Binders used to treat the fibers broadly include substances which can be applied in liquid form to entrained fibers during treatment. These binder materials are preferably of the type which are capable of subsequently binding the fibers produced by the process to one another or to other fibers during the manufacture of webs and other products using the treated fibers. Most preferably these binders comprise organic polymer materials which may be heat fused or heat cured at elevated temperatures to bond the fibers when the fibers are used in manufacturing products. Also, in applications where solid particulate material is to be adhered to the fibers by the binder, the binder must be of a type which is suitable for this purpose.

Suitable binders include polymeric materials in the form of aqueous emulsions or solutions and nonaqueous solutions. Chitosan starches and waxes are also suitable binders. To prevent agglomeration of fibers during the treatment process, preferably the total liquid content of the treated fibers during treatment, including the moisture contributed by the binder together with the liquid content of the fibers (in the case of moisture containing fibers such as wood pulp), must be no more than about forty-five to fifty-five percent of the total weight, with a twenty-five to thirty-five percent moisture content being more typical. Assuming wood pulp is used as the fiber, the moisture contributed by the wood pulp can be higher, but is preferably less than about ten to twelve percent and more typically about six to eight percent. The remaining moisture or liquid is typically contributed by the binder. These polymer emulsions are typically referred to as "latexes." In the present application, the term "latex" refers very broadly to any aqueous emulsion of a polymeric material. The term solution means binders dissolved in water or other solvents, such as acetone or toluene. Polymeric materials used in binders in accordance with the present method can range from hard rigid types to those which are soft and rubbery. Moreover, these polymers may be either thermoplastic or thermosetting in nature. In the case of thermoplastic polymers, the polymers may be a material which remains permanently thermoplastic. Alternatively, such polymers may be of a type which is partially or fully cross-linkable, with or without an external catalyst, into a thermosetting type polymer. As a few specific examples, suitable thermoplastic binders can be made of the following materials:

ethylene vinyl alcohol
polyvinyl acetate
polyvinyl alcohol
acrylic
polyvinyl acetate acrylate
acrylates
polyvinyl dichloride
ethylene vinyl acetate
ethylene vinyl chloride
polyvinyl chloride
styrene
styrene acrylate
styrene/butadiene
styrene/acrylonitrile
butadiene/acrylonitrile
acrylonitrile/butadiene/styrene
ethylene acrylic acid
polyethylene
urethanes
polycarbonate
polyphenylene oxide
polypropylene
polyesters
polyimides In addition, a few specific examples of thermoset binders include those made of the following materials:
epoxy
phenolic
bismaleimide
polyimide
melamine/formaldehyde
polyester
urethanes
urea
urea/formaldehyde Wax, starch and chitosan are yet additional examples of suitable binders. However, as explained below, although starch is a suitable binder for attaching particles to fibers, it has not been found to provide a substantially continuous coating on fibers.

As explained more fully below, in accordance with the method of the present invention, more than one of these materials may be used to treat the discontinuous fibers. For example, a first coating or sheath of a thermoset material may be used followed by a second coating of a thermoplastic material. During subsequent use of the fibers to make products, the thermoplastic material may be heated to its softening or tack temperature without raising the thermoset material to its curing temperature. The remaining thermoset material permits subsequent heating of the fibers to cure the thermoset material during further processing. Alternatively, the thermoset material may be cured at the same time the thermoplastic material is heated by heating the fibers to the curing temperature of the thermoset with the thermoplastic material also being heated to its tack temperature.

Certain types of binders enhance the fire resistance of the treated fibers, and thereby of products made from these fibers. For example, polyvinyl chloride, polyvinyl dichloride, ethylene vinyl chloride and phenolic are fire retardant.

Surfactants may also be included in the liquid binder as desired. Other materials, such as colorants or dyes, may also be mixed with the liquid binder to impart desired characteristics to the treated fibers. If a water insoluble dye is included in the binder, the dye remains with the fibers, rather than leaching into aqueous solutions used, for example, in wet laying applications of the treated fibers. Also, dye would not leach from towels and other products made from these fibers when these products are used, for example, to wipe up liquids. Solid particulate materials, such as pigments, may also be mixed with the binder for simultaneous application with the binder. In this case, the particulate material is typically coated with the binder rather than having exposed uncoated surfaces when adhered to the fibers as explained below. Other liquid materials may also be mixed with the binder with the mixture still performing its function.

In addition, in accordance with the invention, one or more solid particulate materials may be adhered to the fibers to provide desired functional characteristics. The solid particulate materials are typically applied to a binder wetted surface of the fibers and are then adhered to the fibers by the binder as the binder dries.

In general, there are several parameters which are believed applicable to the selection of a suitable binder for binding a particulate to a fiber. The first parameter involves the proper functionality of the binder. In the case of particulate materials, such as super absorbent polymers and other polar, hydrophilic materials, proper functionality amounts to some functionality in the binder surface structure which is capable of hydrogen bonding to like functionalities on the surface of the particulate. Examples of such functionalities would include carboxyl groups, hydroxyl groups, amino groups and epoxides. In the case of non-polar, hydrophobic particles, proper functionality amounts to correspondingly non-polar hydrophobic portions on the binder surface structure, capable of manifesting a van der Waals' attraction to similar portions on the surface of the particles. In addition to functionality, another parameter believed important in the selection of a binder is that of good intermolecular contact between the binder and particles. That is, the functionalities of the first parameter are preferably juxtaposed in a manner close enough for significant interaction (hydrogen bonding or van der Waals' attraction) to occur. In this case, surfactants/emulsion systems of various latexes can be important in binding certain particulates. The surfactants serve to reduce contact angles between the binder and particulates, thus promoting or inhibiting the requisite intermolecular contact. As a third parameter in the selection of a binder, it is desirable that the binder be persistent. Water would be an excellent binder of super absorbent particles if it were persistent, as it satisfies the initial two criteria. However, water is a poor binder of super absorbent particles because it is not persistent. More persistent compounds (e.g. starch, PEG, HEC, CMC and so forth) with similar functionalities do make good super absorbent particle binders. The above parameters seem to also apply to thermoplastic and thermoset binders as well as other types of binders. Although the invention is not limited to a particular theory, selection of binders suitable for attaching specific particles to specific fibers may be made by keeping these parameters in mind. In this case, heat curing or heat fusing of the binder is not required to adhere the particles to the fibers.

Although not limited to specific materials, examples of suitable particulate materials include pigments and whiteners, such as inorganic pigments including titanium dioxide, ferrous oxide, PbO, AlO and $CaCO_3$ ($CaCO_3$ can also function as a filler in paper making applications and is not as white of a pigment as $TiO_2$) and organic pigments or colorants, such as Morton Hytherm Purple KI from Morton Thiokol Company of Chicago, Ill.; ultraviolet, infrared or other wave length blocking or inhibiting particulates, such as carbon blacks as an ultraviolet inhibitor and zirconium carbide as an infrared inhibitor; fire retardant materials, such as alumina trihydrate, antimony oxide, chlorinated and brominated compounds, pentabromochlorocyclohexane, 1,2-Bis (2,4,6-tribromophenoxy) ethane, decabromodiphenyl oxide, molybdenum oxide and ammonium flyroborate, etc.; electrically conductive materials, such as metallic powders and carbon black; abrasive materials, such as ceramics, grit and metallic powders (with flint, garnet, sand, corundum, silicon carbide and stannous oxide, fly ash, stellite and silica being specific examples); acidular materials, such as clay, talc and mica, used as papermaking additives; oleophilic materials such as polynorbornene and fumed silica; hydrophobic materials; and hydrophilic materials, such as hydrophillic silica (e.g. silane treated foamed silica) and super absorbent particles; pesticides and insecticides, such as GUTHION TM insecticide (O, O-dimethyl S-4-0×0-123-benzotriazin-3-(4H)ylmethyl phosphorodithioate, etc.; fertilizers; seeds; antimicrobial particulates, such as broad spectrum antimicrobials (e.g. hypochlorites, perborates, quaternary ammonium compounds, bisulfites, peroxides, etc.), narrow spectrum antimicrobials (e.g. chloramphenacol, 1-[2,4-dichloro-$\beta$-(2,4-dichlorobenzyloxy) phenethyl] imidazole nitrate, [1-(o-chloro $\alpha$, $\alpha$-diphenyl benzyl) imidazole, etc.), antivirals, antimycotics, antibacterials, antirickettsials, antibiotics, biocides, biostats, etc., and mixtures thereof; molecular sieves, such as odor absorbing sieves (ABSCENTS TM, e.g. sodium alumino silicates), drying agents (molecular sieves, magnesium sulfate, sodium sulfate, etc. and activated carbon); zeolites, e.g. based upon alumino phosphates and which may be modified to have antimicrobial properties; acids and bases, for example to alter the pH of a hazardous spill (ammonium chloride, aluminum sulfate, calcium carbonate, sodium bicarbonate, etc.; fiber appearance modifiers, such as mica, phosphorescent compounds (e.g. luciferin/luciferase, zinc sulfide/manganese); microspheres, including microencapsulated particles comprising time release microspheres which may contain a variety of chemicals, such as fertilizers and perfumes; microsponges, with or without added chemicals for functionality purposes; odor absorbing, inhibiting and masking particles such as activated carbon and perfumes (e.g. anisyl alcohol, benzophanone, musk and ABSCENTS TM mentioned above); fungicides (which may be broadly considered as an antimicrobial), such as misonazole nitrate and CAPTAN TM fungicide (trichloromethythio-dicarboximides), etc.; electromagnetic absorbers/deadeners (e.g. Fe, Pb, Al, Ag, Au); flame enhancers, such as powdered magnesium; magnetizing particulate materials, such as iron oxides; heat release particles, such as PEG-1000 (polyethylene glycol) which may be used in handwarmers and which crystalize at room temperature; radioactive particle tracers or labels, such as Carbon 14 (which may for example be combined in a bandage to trace absorption of antimicrobials from the bandage into a user's body), sodium iodide, uranyl nitrate, thorium nitrate, etc., starch particles such as cationic size press starch, which can be a binder when wet and can serve as a biodegradable adhesive; granular polymer particulate materials, such as recycled thermoset or thermoplastic polymer particles, which may, for example, be used as a filler when attached to fibers; catalysts, such as finely divided platinum; radar reflective particles, such as metallic powders; radar absorbing particles, such as graphite and ferrites; sound deadening or absorbing particles, such as barium sulfate; antistatic particles, such as sulfonated polyaniline and electrically conductive particles (e.g. metal powders); hot melt adhesives, such as ethylene vinyl acetate (these particles may have either higher or lower melting points than heat fusable or curable binders if used to attach the particles to fibers); bulking agents, such as expanded or unexpanded microspheres, ground foams, hi-bulk silicas, etc.; lubricating (antifriction) particulates, such as graphite and TEFLON TM particles; friction inducing particulates, such as rubber; powdered soaps, surfactants and degreasers, such as laundry detergent (e.g. sodium dodecyl sulfate); chitosan particles; pollutant filtering particles, such as polyethyleneimine as a powder or a particulate for formaldehyde filtering; sorbants, such as diatomaceous earth; a coagulant or blood clotting agents (such as incorporated into bandages) with calcium nitrate being one example; indicators, such as for indicating the presense of chemicals (e.g. phenolphthalein/bromothymol blue) and water (e.g. cobalt chloride); anesthetic or pain killing particles (such as incorporated into dressings) with acetaminophen and codeine being specific examples; dissicants, such as calcium sulfate; medicines and pharmaceuticals, such as cortisone (antiinflammatory), DRAMAMINE TM medication, nitroglycerine; chemical neutralizing particles, such as potassium permanganate for neutralizing formaldehyde; oxidizing agents, such as potassium permanganate; reducing agents, such as aluminum; fabric softeners, such as quaternary ammonium salts and cationic surfactants; nutrient particles, such as vitamins, with ascorbic acid being a specific example of such particles (which would also function as a food preservative); and blood anticoagulants, such as heparin. Thus, the solid particulate materials are not limited to narrow categories. Furthermore, one or more of the above particles may be mixed as required. When mixed, multiple types of particles may be adhered to the same fibers. Alternatively, blends of fibers, each with one or more particle types may be used. Also, the specific examples listed in the categories identified above are by no means exhaustive nor are the identified particulate categories intended to be limiting. These fibers with attached particulate materials may be included in absorbent and other structures, such as filters and rigid structures, and may or may not be blended with other fibers (including wood pulp fibers) in such structures.

The super absorbent particulate materials are granular or powdered materials which have the ability to absorb liquids, including body fluids. These super absorbents are generally hydrophilic polymeric materials. Super absorbents are defined herein as materials which exhibit the ability to absorb large quantities of liquids, i.e. in excess of ten to fifteen parts of liquid per part thereof. These super absorbent materials generally fall into three classes, namely, starch graft copolymers, cross-linked carboxymethyl cellulose derivatives and modified hydrophilic polyacrylates. Without limiting the generality of the term super absorbent, examples of super absorbents include carboxylated cellulose, hydrolyzed acrylonitrile-grafted starch, acrylic acid derivative polymers, polyacrylonitrile derivatives, polyacrylamide type compounds, saponified vinyl acetate/methyl acrylate copolymers, and blood specific super absorbent particles (such as TYLOSE TM 3790 blood specific superabsorbent particles from Hoeschst-Celanese, Inc. of Portsmouth, Va.). Specific examples of super absorbent particles are marketed under the trademarks "SANWET" (supplied by Sanyo Rasei Kogyo Kabushiki Kaisha) and "SUMIKA GEL" (supplied by Sumitomo Kagaku Kabushiki Kaisha).

An abrasive is a hard substance that, in particulate form, is capable of effecting a physical change in a surface, ranging from the removal of a thin film of tarnish to the cutting of heavy metal cross sections and cutting stone. Abrasives are used in scores of different abrasive products. The two principal categories of abrasives are: (1) natural abrasives, such as quartz, emery, Carborundum, garnet, tripoli, diatomaceous earth (diatomite), pumice, and diamond; and (2) synthetic abrasives, such as fused alumina, silicon carbide, boron nitride, metallic abrasives, and synthetic diamond.

Oleophilic materials are those capable of rapid wetting by oil while hydrophilic materials are those capable of rapid wetting by water.

Pigments or colorants can broadly be defined as being capable of re-emitting light of certain wavelengths while absorbing light of other wavelengths and which are used to impart color.

Electrically conductive materials are those which readily conduct electrical current.

In addition, fire retardant materials are those which reduce the flammability of the fibers to which they are attached. Preferably these materials are active fire retardants in that they chemically inhibit oxidation or they emit water or other fire suppressing substances when burned.

With reference to FIG. 1, a sheet of chemical wood pulp 10 is unrolled from a roll 12 and delivered to a refiberizing apparatus, such as a conventional hammer mill 14. The sheet 10 is readily converted into individual fibers 16 within the hammer mill. These individual fibers are delivered, as by a conveyor 18, to a fiber loading zone 20 of a fiber treatment apparatus. In the case of a continuous process, fibers 16 are continuously delivered to the zone 20. In a batch or semi-batch process, fibers are loaded at zone 20 at intervals.

In the FIG. 1 fiber treatment apparatus, loading zone 20 forms part of a fiber treatment conduit 24. The illustrated conduit 24 comprises a recirculating loop. A blower or fan 26 in loop 24 is positioned adjacent to the fiber loading zone 20. Blower 26 is capable of moving a gaseous medium, such as air, at a velocity and volume sufficient to entrain the fibers which have been loaded into zone 20. The entrained fibers circulate in a direction indicated by arrow 28 through the loop and pass through the loading zone 20 and blower 26 each time the loop is traversed.

The velocity of air traveling in the loop is preferably set at a level where solids are uniformly dispersed and transported by the air flow. In addition, the velocity is preferably established at a level which is sufficient to avoid saltation, that is the dropping of solids or liquids from a horizontal air stream. As a specific example, when Type NB316 chemical wood pulp, available from Weyerhaeuser Company, was used as the fiber, a velocity of 5,000 feet per minute worked extremely well for treatment of these fibers in accordance with the method. However, this velocity can be varied and adjusted for optimum results.

Also, the ratio of the volume of air per pound of entrained fiber is variable over relatively large ranges. One suitable example is 23.4 $ft^3$ of air per pound of fiber. As another example, 11.7 $ft^3$ of air per pound of fiber produced equivalent results.

The entrained fibers traveling in the loop pass one or more binder material application zones, with one such zone being indicated in FIG. 1 at 30. This binder material application zone 30 forms a part of the conduit 24. A mechanism is provided at the binder application zone for applying a liquid binder solution or emulsion to the entrained fibers. In the FIG. 1 form of this mechanism, plural nozzles, in this case nozzles 32, 34 and 36, are used to apply the liquid binder material. These nozzles produce an atomized spray or mist of binder drops which impact and coat the fibers as the fibers pass the nozzles.

In the FIG. 1 apparatus, plural valves 40, 42 and 44 are operated to control the flow of liquid binder material to the respective nozzles 32, 34 and 36. In the illustrated configuration, a first liquid binder material from a tank or other source 46 is delivered to the three nozzles 32, 34 and 36 when valves 40 and 42 are open and valve 44 is closed. As the fibers recirculate through the conduit 24, and each time they pass the nozzles, an additional amount of the first liquid binder material is applied. Different surfaces of the fibers are exposed to the nozzles 32, 34 and 36 as the fibers travel through the material application zone 30. After the desired amount of the first liquid binder material is applied, the valve 40 is closed. If desired for a particular application, a second liquid binder material from a tank or other source 48 may also be applied to the fibers. With valves 42 and 44 open and valve 40 closed, this second liquid binder material is applied to the fibers through each of the nozzles 32, 34 and 36. In addition, the two liquid binder materials may be simultaneously applied, at successive locations in zone 30. For example, the valve 42 may be closed and valve 44 opened so that the first liquid binder material is applied through nozzles 32, 34 and the second liquid binder material is applied through nozzle 36. More than two types of liquid binder materials may be applied by adding additional binder sources and suitable valving and nozzles.

In general, the material application zone 30 typically ranges from two to one hundred feet long, with longer application zones allowing the application of binder over a longer period of time during passage of fibers through the material application zone. Also, longer material application zones facilitate the use of more nozzles spaced along the length of the zones.

The nozzles 32, 34 and 36 are commercially available and produce a fine mist of droplets. Typically, these nozzles provide a fan spray. Any suitable nozzles may be used, but it is desirable that the nozzles not produce a continuous stream of liquid binder material, but instead produce droplets or a mist of such material. The nozzles are typically spaced apart from three to four feet along the length of the conduit, although they may be closer or further apart as desired.

Virtually any amount of binder material may be applied to the entrained fibers. However, it has been found that the application of binder must be at a minimum of about seven percent of the dry weight of the combined fibers and binder in order for the fibers to have a substantially continuous sheath or coating of the binder material. If the fibers lack a continuous coating, it becomes more difficult to adhere significant amounts of particulate material to the binder in the manner explained below. In fact, a much higher percentage of binder than this minimum is preferably used to adhere particles to the fibers. Also, exposed portions of the core fiber, that is surface areas of the fiber not coated with the binder, lack the desired characteristics of the binder. For example, if a hydrophobic binder is used to cover a water absorbing cellulose material, failure to completely enclose the material with the coating leaves exposed surfaces of the fiber which can absorb water. Also, any uncoated areas on the fibers would not bond to other untreated fibers during subsequent heat bonding of the treated and untreated fibers.

The binder provides a coating over a substantial majority of the surface area, meaning at least about eighty percent of the surface area of the individual fibers. More typically, the fibers are substantially continuously coated with a continuous binder coating over substantially the entire surface (at least about ninety-five percent of the surface area) of the individual fibers. Also, in many cases virtually all of the surface area of the individual fibers is continuously coated, meaning that the surface coating is an unbroken and void free, or at the most has a few voids of less than the diameter of a fiber.

Also, binder may be applied so that a substantial majority of the fibers, that is at least eighty percent of the fibers: (a) have a substantial majority of their surface area coated; (b) a substantially continuous coating; or (c) have virtually their entire surface continuously coated. The remaining fibers typically have varying degrees of coating ranging from discrete patches of coating to a major portion of their surface (fifty percent or more) being continuously coated. Variations occur due to the type of binder being applied, the loading of the binder, and the fact that not all of the fibers receive the complete treatment. Also, substantially all (at least about ninety-five percent) of the individual fibers and fiber bundles being treated in bulk have been produced with coatings falling into the above three categories. Of course, for many applications it is desirable that substantially all of the fibers of the bulk fibers being produced have a substantially continuous coating or virtually their entire surface continuously coated because, in this case, the characteristics of the binder (as opposed to exposed fiber surfaces) controls the properties of the fibers. It has also been found that binder loading levels of approximately about seven percent of the combined weight of the binder and fiber results in fibers a substantial majority of which, and more typically substantially all of which, have a substantially continuous coating.

In addition, the continuous coating is extremely uniform over the coated surface of the fibers and fiber bundles. For instance, a fiber coated with twenty percent by weight binder, such as polyethylene (PRIMACOR binder), to the combined weight of the binder and fibers of a binder, forms a coating which is about 0.5 microns thick, plus or minus about 0.25 micron. If the coating add-on were 40% by weight of this binder to the weight of the binder and fibers, then the coating thickness would be about 1.0 micron, plus or minus 0.25 micron.

It has also been found that, with a binder concentration of about ten percent by dry weight of the weight of the fiber and binder combination, the fibers, when heat fused, will bond somewhat strongly to other fibers coated in a similar manner, but less strongly to untreated fibers. The resulting bond strength is similar to the strength achieved when fibers coated with a forty percent by dry weight binder amount are mixed with untreated fibers in a ratio of one part treated fiber to three parts untreated fiber. A binder concentration by dry weight of the combined binder and fibers of from thirty percent to fifty percent has proven extremely suitable for use in mixing with other fibers, heat bonding, and use in forming products such as absorbent pads.

Binder concentrations in excess of fifty percent, for example ninety percent or more, can be achieved utilizing the present invention. To achieve these extremely high binder concentrations, one preferred approach is to apply a first amount of the binder material to the entrained fibers, continue to recirculate the fibers until this first layer or coating of binder material is substantially dry, and then apply a second coating of the binder material. Third, fourth and subsequent coatings can be applied to the entrained fibers as necessary to achieve the desired level of binder material.

Following the application of the liquid binder material to the fibers, the fibers may be retained in the loop until they have dried. The recirculation of the fibers may then be stopped and the fibers removed at the loading zone 20 which then functions as a fiber removal location. However, in the FIG. 1 apparatus, a cyclone separator 60 is selectively connected by a conduit section 61 and a gate valve 62 to the conduit 24. At the same time a valve 64 is opened to allow air to enter the loop 24 to compensate for air exiting through the separator 60. With the separator in the loop, the entrained fibers are collected in the separator and then removed from the separator at a fiber removal outlet 66. A substantial majority of the fibers processed in this manner are unbonded to one another by the binder material. By substantial majority, it is meant that at least about seventy percent of the fibers remain unbonded. More specifically, in tests conducted as of this time, the resulting treated fibers are substantially unbonded, meaning that approximately ninety-five percent of the treated fibers have been found to be unbonded to one another by the binder material.

An optional means for heating the binder coated fibers may be included in conduit 24. For example heated air may be blended with the air flowing through the conduit. Similarly, a heater 70 may be included in conduit 24 for heating the fibers. This added heat accelerates the drying of the liquid binder. In the event a thermoplastic heat fusible binder is used, the fibers are preferably heated above the film forming temperatures of the binder and below the hot tack temperature at which the binder becomes tacky so that the binder coated fibers may subsequently be heat fused during processing of the fibers into products. Also, if a thermoset heat fusible binder is used, the fiber temperature is preferably maintained below the curing temperature of the binder so that the binder coated fibers may be subsequently heat cured during the processing of the binder coated fibers into products.

The fibers are preferably not heated prior to the application of the binder material. It has been found that heating the fibers results in elevated temperatures at the binder application zone 30. These elevated temperatures cause some of the binder to at least partially dry (coalesce) before reaching surfaces of fibers passing through the binder application zone 30. The solidified binder either does not adhere, or only adheres weakly to the fibers. In addition, droplets of binder which impinge heated fibers tend to dry in globules on the fibers, rather than spread across the surface of the fibers to provide a substantially continuous uniform coating thereon.

The dried fibers from outlet 66 of the cyclone separator 60 may be deposited in a conventional baling apparatus 72. To prevent bonding of the fibers in the baler, the fibers are at a temperature which is below their curing or tack temperature under the pressure applied by the baler. When compressed, these fibers remain unbonded by the binder material and therefore can be readily separated into individualized fibers for subsequent use.

Also, treated fibers which have only been partially dried, and thus which are still somewhat wet with the binder material, may be deposited from outlet 66 loosely onto a conveyor 74 or in a loose uncompressed pile at a collecting zone (not shown). These fibers can then be allowed to dry. Alternatively, the treated fibers may be carried by the conveyor 74 through a heater 76 to accelerate the drying of the fibers. The resulting product again contains a major portion of unbonded fibers. However, the wetter the fibers and more dense the resulting web when deposited on belt 74, or in a pile, the more binder-to-binder bonds that occur. Thus, in many cases it is preferable to at least partially dry the fibers within the conduit 24 prior to removing the fibers therefrom. However, the fiber may be air laid either dry or wet, that is with no more than about a 55 percent total moisture content in the fibers and binder thereon, directly into a web which can then be processed into various products, such as absorbent structures of various types, including disposable diapers with the core of the diaper being formed by the web. Air laying refers to the transfer of the fibers through air or another gaseous medium and depositing of the fibers onto a screen or other form.

Solid particulate materials, such as super absorbent particles and other materials, may be adhered to the fibers by the binder material. To accomplish this, the solid particulate material is added to the loop 24, such as at the fiber loading zone 20. The particles may also be added to the loop 24 from a supply housing 80, using a feed screw metering device or other conventional injection mechanism. Preferably, the particles are added after the fibers have been wetted with the binder material. Consequently, the particles will not be covered with the binder material, which could interfere with the desired attributes contributed by the particles. These particles contact the wet binder material on the surfaces of the fibers and stick to the binder material. As the binder material dries, the particles remain stuck to the surface of the treated fibers. In one specific approach, the fibers are treated with a binder, circulation of the fibers is stopped momentarily to allow the addition of the solid particulate material at the fiber loading zone 20, and recirculation and entrainment of the fibers is recommenced. The particles mix with and are secured to the surface of the fibers by the liquid binder material as the binder dries. Although lower concentrations are effective in binding particles to fibers, it has been found that relatively high levels of binder concentrations, for example twenty percent or more of the dry weight of the binder, fiber and additive, produces the best adhesion of particles to the fibers. A fifty percent binder concentration would perform better in adhering particles to the fibers than a twenty percent binder concentration in many applications. These higher binder levels, when heat fusible binders are used, facilitate subsequent heat fusion of the fibers and strong bonding, with or without other fibers being added, during use of the fibers in manufacturing absorbent structures or other products. However, lower binder content may be used to reduce the possibility of the binder coating the particles and interfering with the functionality of the particles.

The FIG. 1 apparatus may be operated in a batch mode in which fibers are introduced, fully treated and removed. Alternatively, a semi-batch approach may be used in which fibers are added and some, but not all, of the fibers removed from the loop. Also, the FIG. 1 apparatus may be operated in a continuous mode in which fibers are introduced at zone 20 and removed by the cyclone separator 60 with or without recirculating through the loop. The gate valves 62, 64 may be opened to a desired extent to control the amount of fiber that is removed. This quantity of removed fiber is preferably equal to the amount of untreated fiber that is introduced into the loop. In this nonrecirculating case, the zone 30 is typically expanded. Also, plural recirculating loops 24 etc. can be provided with respective loading zones 20 etc. and outlet conduits 61. These loops, loading zones and outlet conduits can be like the apparatus of FIG. 1. The fibers are selectively and automatically delivered to the loading zones, as via conduits from a fiberizing device to maximize the volume of fibers being treated. For example fiber can be added to one loop 24 while fiber is being treated in another loop and being removed from a third loop. Thus a single source of fiber and mechanism for removing treated fibers may be used in combination with plural loops.

Figure 2:
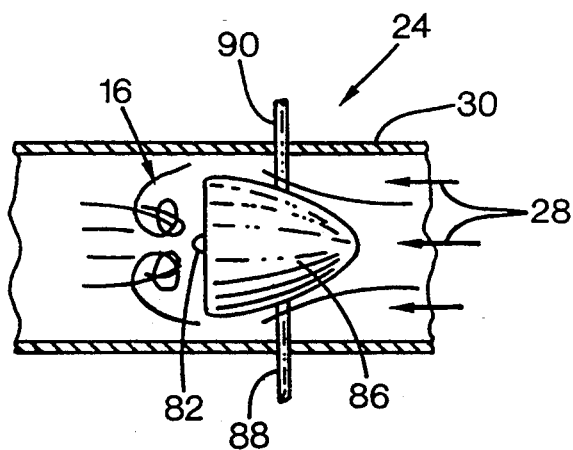
FIG. 2 is a side elevational section view of one form of binder application mechanism which can be used in the apparatus of FIG. 1 to apply liquid binder material to discontinuous fibers in accordance with the method of the present invention.
Figure 3:
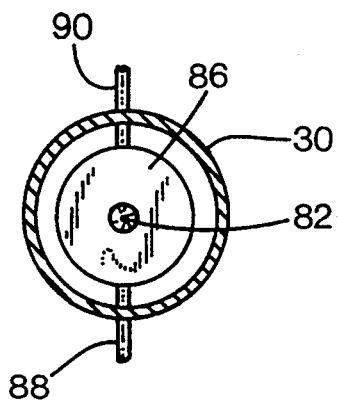
FIG. 3 is a front elevational section view of the binder application mechanism of FIG. 2.

With reference to FIGS. 2 and 3, another mechanism for applying binder material to the fibers is illustrated. Rather than using external spray nozzles such as 32, 34 and 36, plural nozzles (i.e., one being shown as 82 in FIGS. 2 and 3) are included in the conduit at the binder material applying zone 30. The nozzle 82 applies a fine spray of liquid binder material onto the fibers 16 as they move past the nozzle. The FIGS. 2 and 3 binder applying mechanism includes a means for imparting turbulence to the air as it passes the nozzles. As a result, the fibers 16 tend to tumble in front of the nozzles and expose different surfaces to the applied binder material. The illustrated turbulence imparting mechanism comprises a blunted conical air deflection baffle 86 supported within the conduit 24 by rods, with two such rods 88 and 90 being shown. Rod 90 may be hollow to provide a pathway through which binder material is delivered to the nozzle 82. Of course, other turbulence imparting mechanisms may also be used.

Figure 4:
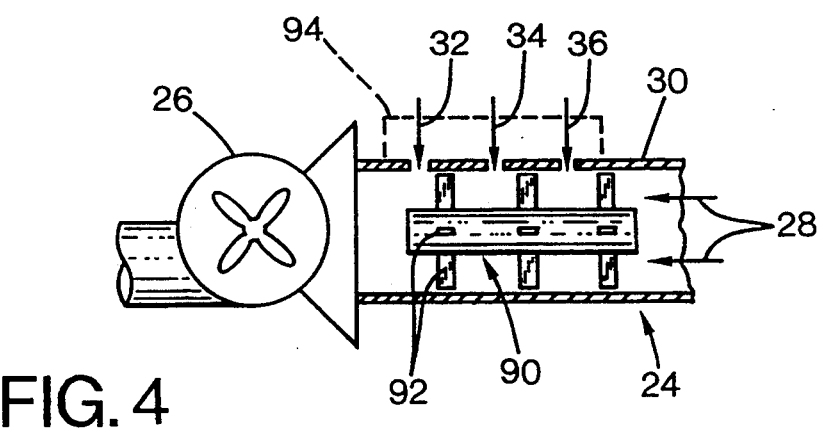
FIG. 4 is a schematic illustration of another form of binder application mechanism which can be used.

In FIG. 4, a rotary mixer 90 with plural mixing paddles, some being indicated at 92, is disposed within the conduit 24 at the material applying zone 30. This mixer is rotated by a motor (not shown) to impart turbulence to fibers as they pass the mixer paddles. The nozzles 32, 34 and 36 are disposed externally of the conduit 24 for directing the binder material through ports to the fibers passing the mixer. These nozzles may be enclosed in a shroud or cover as shown by dashed lines 94 in this figure. However, in the FIG. 4 approach, blower 26 has been shifted to a location downstream from the material applying zone 30. Consequently, the material applying zone is at a relatively low pressure with a slight vacuum being present in the material applying zone relative to the pressure outside the conduit at this zone. Consequently, fibers passing the nozzles 32, 34 and 36 tend to be drawn into the conduit rather than escaping through the binder applying ports. As a result, the nozzles can be positioned outside of the conduit where they are not subject to being clogged by the passing fibers.

Figure 5:
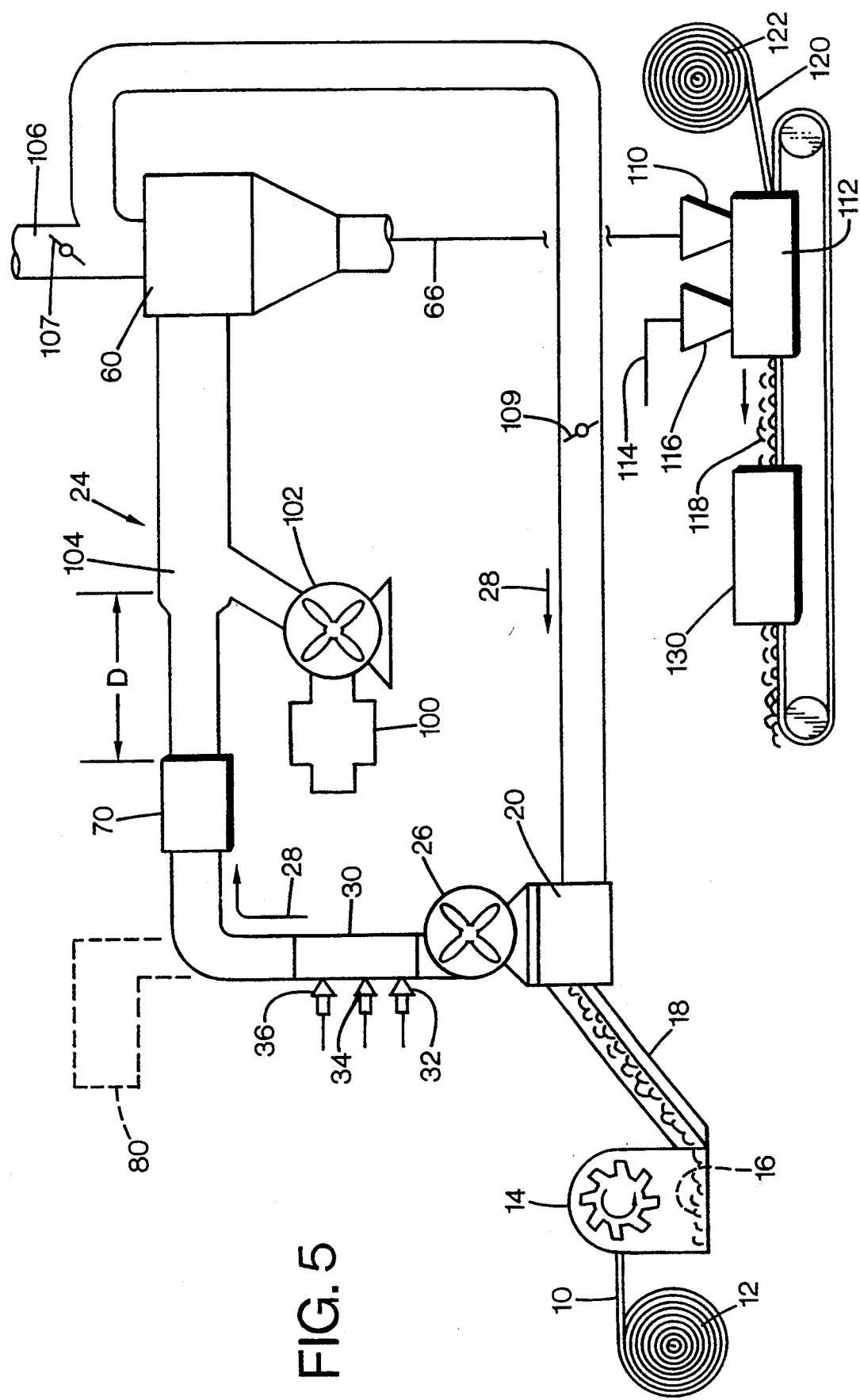
FIG. 5 is a schematic illustration of another apparatus usable to obtain fibers of the present invention.

Referring to FIG. 5, another apparatus is shown for producing fibers of the present invention. In FIG. 5, for purposes of convenience, elements in common with those of FIG. 1 have been given like numbers and will not be discussed in detail.

In general, the FIG. 5 form of the apparatus allows the continuous processing of fibers with the fibers passing only once through the binder material application zone 30. However, the zone 30 is typically of an extended length with more nozzles (i.e. six to twelve or more) than shown in FIG. 5. Following the application of the binder material, solid particulate material may be added from source 80, such as by a blower (not shown) or a feed screw, to introduce the particles into the stream of entrained fibers. The fibers pass through a heater or oven 70, or heated air is blended with the air stream which entrains the fibers, for drying purposes and then travel through a distance D at the elevated temperatures created by this heat. As a typical example, D may be 150 feet with the time required to travel the distance D enabling the binder on the entrained fibers to become substantially dry. Optionally, cooling air from a refrigeration unit 100 or ambient air from the environment may be delivered by a blower 102 to the conduit 24 at a location 104 in the conduit. This cooling air lowers the temperature of the dried and treated fibers. The cooling air may be dehumidified prior to introduction to conduit 24 to minimize any condensation that may otherwise occur in the conduit. Where thermosetting binders are used, preferably the added heat does not elevate the temperature of the fibers to a level which cures the thermosetting binder. Consequently, the binders may subsequently be heat cured when the treated fibers are thereafter used in manufacturing. Also, where thermoplastic binders are used, the temperature is preferably kept above the film forming temperature and below the hot tack temperature of the thermoplastic binder material. Cyclone separator 60 may be provided with a bleed line 106 for venting the air during separation. Although less preferred, this air may be recirculated back to the fiber-loading zone 20. Flow control gate valves 107, 109 may be included in the system to balance the air flow through the various conduits of the illustrated system.

The treated fibers from outlet 66 of the separator 60 may be fed to a hopper 110 of a conventional fiber blending unit 112. Other fibers, such as wood pulp fibers or synthetic fibers are fed, in a desired proportion for the resulting product, by way of a conduit 114 to another hopper 116 and then to the blending unit 112. The fibers from outlet 66 can also be used without blending them with other fibers. The blended treated and untreated fibers 118 are shown being deposited on a facing sheet 120 which is passed through the blending unit 112 from a roll 122. The fibers may also be deposited directly on a conveyor without a facing sheet. The facing sheet is carried by a conveyer 124 through the blending unit 112. The composite web is then passed through a thermobonding unit 130 which raises the temperature of the fibers sufficiently to cause the treated fibers to heat fuse to the other fibers and to the facing sheet. The fibers may be compressed to densify the web prior to or after delivery to the thermobonder 130. A cover sheet may also be added to the product before or after the thermobonder 130. Following thermobonding, to reduce the stiffness of the webs, they may be "tenderized" by the use of a mechanism which mechanically breaks up some of the bonds in the web. The web still remains substantially bonded, however. As one example, the webs may be passed through the nips of cross machine direction and machine direction corrugators to reduce their stiffness. The stiffness can be controlled by adjusting the clearance between the nips. Although not limited to a specific approach, examples of suitable corrugators and tenderizing procedures are disclosed in U.S. Pat. Nos. 4,559,050; 4,596,567 and 4,605,402. The resulting material can be used in a conventional manner to manufacture a wide variety of products, such as absorbent pads, disposable diapers, webs and the like.

The following examples will serve to more specifically illustrate the fiber product of the present inven-

EXAMPLE 1

A bleached Kraft Southern Pine cellulose fiber pulp sheet (NB-316 from Weyerhaeuser Company) was fiberized in a hammer mill. One kilogram of the fiberized fluff was then air entrained in a recirculating conduit. After 20 seconds of air entrainment, 1223 grams of PRIMACOR 4990 ethylene acrylic acid copolymer solution, 35 percent solids, was sprayed onto the air entrained fiber over a period of eight minutes. PRIMACOR 4990 binder is available from Dow Chemical Corporation. The coated fiber was then recirculated for two minutes prior to separation in a cyclone. The still somewhat wet coated fiber was then deposited in a loose pile and air dried at room temperature for 24 hours. Even though wood fibers are of irregular cross-section and thus more difficult to coat than surfaces with a regular cross-section or smooth surface, the resultant fibers had a uniform continuous coating of binder. Also, approximately ninety-five percent of the fibers were unbonded to one another by the binder material. The dried fiber was then easily air laid in a laboratory pad former. Six inch diameter pads weighing ten grams were prepared. These pads were then compressed in a press to densities of from 0.04 to 0.15 g/cm$^3$ and then thermobonded at 140 degrees Centigrade in an air-through laboratory bonding unit. The resulting pads were tested for tensile index (tensile strength in N/m divided by basis weight in g/m$^2$). The tensile index was 0.6 N-m/g for pads having a density of 0.06 g/cc.

In addition, the dried coated fiber obtained in this manner was blended with uncoated fiber in a ratio of ⅓ coated fibers to ⅔ uncoated NB-316 fibers. The blend was air laid and thermobonded. The tensile index of the blend was 0.3 N-m/g at a 0.06 g/cc density. PRIMACOR binder is a hydrophobic, somewhat oleophilic thermoplastic binder. Therefore, a PRIMACOR binder coated fiber is capable of absorbing oil and excluding water.

A wide variety of other binders have also been tested, including SYNTHEMUL 40-800 and 40-850 emulsions, available from Reichhold Chemical Corporation. Cellulose fibers having five percent, seven percent, ten percent, twenty percent, thirty percent and fifty percent by dry weight SYNTHEMUL 40-800 binder coating have been manufactured using the present method. It is only at levels of about seven percent that a continuous coating of the fibers is achieved. At five percent, the binder material was present as non-interconnected areas or blobs on the surface of the fibers. These percentages are the percent of dry weight of the fiber and binder combination which is the binder. In a recirculating system, to achieve higher percentages of the binder concentration, the fibers were recirculated in the loop during liquid binder application for a longer time. Pads made in the above manner with thirty-five percent and forty-five percent SYNTHEMUL 40-800 binder, respectively, had tensile indices of respectively 1.98 and 1.99 N-m/g at a 0.06 g/cc density. SYNTHEMUL binder is a more hydrophilic binder than PRIMACOR. Also, ELVACE 40-712 binder, available from Reichhold Chemical Corporation, an ethylene vinyl acetate, has also been tested as have a number of other binder materials. These tests have all confirmed that substantially unbonded individualized fibers coated with a substantially continuous coating of binder material can be provided.

EXAMPLE 2

This example is similar to example 1, with the exception that a larger volume of fibers were treated at one time. In addition, a surfactant material was added to the PRIMACOR binder for application with the binder. In this specific example, Aerosol OT-S Dioctyl Sodium Sulfosuccinate seventy and two/tenths percent OT-S, available from American Cyanamid Corporation, was used as the surfactant material. A four kilogram batch of treated NB-316 fluff was processed as explained in example 1. Sufficient PRIMACOR binder was added to generate a mixture that was eighty percent NB-316 wood pulp fibers, twenty percent PRIMACOR binder with one and 74/100 percent surfactant based on the PRIMACOR binder solids. The treated fibers were recirculated in the loop for 15 seconds following the application of the PRIMACOR binder and then dumped in a pile for subsequent drying. Again, substantially unbonded individualized substantially continuously coated fibers resulted.

EXAMPLE 3

Thermoset materials have been used in accordance with example 1 to coat fibers to the desired percentage. For example, a mixture of polymeric methylene diisocyanate (PMDI) resin, such as PAPI 2027 from Dow Chemical Corporation and propylene carbonate from Arco Chemical Corporation can be sprayed onto the fibers. Dioctyl Sodium Sulfosuccinate may be used as a surfactant in this case. CASCOPHEN WC04 resin from Borden Chemical Corporation is a specific example of a suitable phenolic resin. Still another example of a specific thermoset resin is CHEMBOND 2509 resin from Chembond, Inc. However, the invention is not limited to specific thermoset binder materials. Thus, fibers have been introduced into a loading zone 20 and entrained. As the fibers traveled past the material applying zone 30, nozzles applied the thermoset resin to the fibers. To increase the weight percentage of thermoset resin, the fiber was recirculated past the nozzles a plurality of times. Also, the lengths of the material zone and number of nozzles may be extended to enhance the rate at which the fibers are coated.

Again, resin in an amount of at least about seven percent of the resin and fiber combination has been found to be required to provide a continuous sheath or coating of thermoset material. Very high weight percentages of thermoset resin, measured in the same manner, can be achieved with ninety percent and higher concentrations expected.

EXAMPLE 4

In accordance with this example, functional materials in particulate form are adhered to the binder coated fibers. It has been found that a binder concentration of seven percent will adhere some particulate material to the fibers, but at binder concentrations of twenty percent of the total dry weight of the binder, fiber and additives, and higher, much better adhesion occurs. Lower binder content may be used (for example between 7 and 10 percent) reduce the degree to which the particles are embedded in the binder, thereby increasing the exposed surface area of the particles and in many cases their functionality.

Fibers were produced in a recirculating loop of the form shown in FIG. 1. In processing the fibers, a sufficient amount of binder material was added to the air entrained fibers to produce the desired concentration. The recirculation blower was then momentarily turned off and the particulate material was added to the system at the fiber loading zone 20. Recirculation of the materials through the loop was then recommenced to mix the particles with the still wet and entrained fibers. Continued circulation of the fibers resulted in partial drying of the binder and adhesion of the particles to the fibers.

In a first more specific example, fibers coated with twenty percent SYNTHEMUL 40-800 binder (the percentage being the percent of binder in the dry fiber, pigment and binder combination) were mixed with a granular pigment material, specifically titanium dioxide. Various amounts of titanium dioxide have been added to the fibers, including an amount which is sufficient to be fifty percent of the dry weight of the binder, fiber and titanium dioxide combination. This material is useful in paper making processes. $CaCO_3$ is another example of a particulate pigment.

Similarly, fire retardant particulate materials, such as alumina trihydrate and antimony oxide may be adhered to binder treated fibers for use in preparing fire retardant materials, such as pads, paper and other products.

To produce an electrically conductive material, a conductive particulate material (such as sixty to eighty percent by weight of the binder fiber and additive combination) may be adhered to the fibers by the binder. Powdered metallic materials and carbon black are examples.

For use in manufacturing abrasive pads and the like, abrasive particulate materials, such as ceramic powders, metallic powders, or grit, may be secured to the fibers by the binder material.

Also, paper making additives, such as acidular particles of clay, talc, mica and so forth, including $CaCO_3$ may be adhered to the fibers. For example, approximately fifty percent by weight of the binder, fiber and additive content may be made up of these additives.

Oleophilic materials, such as polynorbornene in a desired concentration may be adhered to the fibers. NORSOREX particles from Norsorlor, a division of CdF Chimie of Paris, France, is one example of such a material. Typically a fugitive surfactant is used in this case. Like the other particulate materials, these materials may be added in varying percentages.

Medicinal particles, meaning those which are capable of performing a biological or medicinal function in treating humans or animals may also be adhered to fibers by binders. As with other particulate materials adhered to fibers, these fibers are incorporated into structures, such as absorbent structures, so as to minimize the migration of these medicinal particles away from a region (for example at a wound site) where they are effective. Exemplary medicinal particles include antimicrobial particles (also see example 14 below), coagulants or blood clotting agents, which may be incorporated into bandages, with calcium nitrate being one example, anticoagulants, such as heparin, anesthetics or pain killing particles, which may also be incorporated into wound dressings, codeine being one specific example, and medicines or pharmaceuticals. When bound to the surface of fibers by the binder, these particles substantially retain their medical effectiveness, with their effectiveness being enhanced by minimizing the surface area of the particles in contact with the binder.

Wavelength impacting particles are yet another category of particles which may be attached to fibers by the binder. These particles absorb or reflect energy of particular wavelengths. Examples of these types of particles include ultraviolet inhibiting or blocking particles; infrared inhibiting particles; radar absorbing or reflecting particles; x-ray inhibiting particles, electromagnetic absorbing or deadening particles and sound deadening or absorbing particles. Again, fibers with these attached particles may be incorporated into structures of various types. For example, fibers with radar absorbing particles may be included in composite materials utilized in aircraft. Fibers with x-ray inhibiting particles may be incorporated into fabrics and other materials utilized, for example, near x-ray machines. Fibers with sound deadening particles may be included in fabric coverings or in the interior of panels used in office and other settings for sound absorbing purposes. These are but a few specific examples of the use of fibers with wavelength characteristic modifying particles adhered thereto.

Highly porous particles, such as molecular sieves, microsponges and microspheres adhered to fibers by binders likewise have numerous applications. For example, these materials may contain antimicrobial chemicals, fragrances, or other substances with the fibers being used to bind these particles in an overall structure. Similarly, cleaning, sanitizing and disinfectant particles, such as antimicrobial particles, zeolites, soaps and degreasers may be adhered to fibers and incorporated in product structures for performing their respective sanitizing, disinfecting and cleaning function.

Magnetizing particulant materials, such as iron oxide, may be adhered to fibers. By selectively applying a magnetic field during the processing of these fibers, for example during air laying of these fibers into a web, the orientation and location of these fibers in the web can be controlled. As a result, the properties of these structures may be controlled. For example, another type of particulate material may be adhered to fibers which also have a magnetizing particulate material, the distribution of this other material in the structure being controllable utilizing a magnetic field.

By adhering flame enhancing particles to fibers, and in particular wood pulp fibers, a flammable material is provided for use in applications wherein a rapid generation of heat and fire is desired.

Nutrients, such as vitamins and food particles, may be attached to fibers by the binder. In many of these applications, the fibers, such as cellulose fibers, would constitute a filler or bulk material used as a vehicle for carrying the nutrients. Wood pulp, being biodegradable, is particularly suitable for this purpose.

Hydrophilic materials, such as silane treated foamed silica may be adhered to fibers by the binder for liquid absorption purposes. Materials which release heat under ambient conditions, such as polyethylene glycol may also be adhered to fibers by the binder.

Fiber appearance modifying particles, such as particulate phosphorescent compounds, may also be adhered by binder to fibers. When such fibers are incorporated into structures such as fabric, the properties of the particulate material carry over to the resulting product.

Particle tracers or labels may be also adhered to fibers by the binder. For example, the tracers or labels may comprise radioactive materials useful in marking the structure in which they are incorporated. Also, such tracers may be included in wound dressings for absorption to provide a marker or label for the absorption of these materials, and accompanying antimicrobials or medicines, into an individual. Again, the particulate labels or tracers retain their properties and can be used in any application where suitable, with the fiber assisting in anchoring the particulate tracers in a structure.

Particulate materials such as starch may be adhered to fibers by the binder. The starch particles themselves can be a binder when wet and can serve as a biodegradable adhesive when cooked to subsequently further bind fibers together in a structure or to bind other particulate materials to the fiber.

Neutralizing or pH modifying particles may also be attached to fibers by the binder. When fibers with these particles are used, for example in an absorbent structure, in cleaning up a hazardous waste spill, the particles dissolve from the fiber and modify the pH of the spill to a more neutral level.

Redox particles may also be attached to fibers for facilitating chemical reactions with the oxidizing or reducing agents contributing to chemical reactions when fibers with attached redox particles are used in a fiber processing application.

Catalyst particles may also be adhered to fibers by the binder. The binder thus holding the catalyst particles in place, such as in a catalytic filter, so as to enhance chemical reactions promoted by the catalyst.

Granular polymer particulate materials, such as recycled polymer particles, may be adhered to fibers by the binder. These materials typically would constitute fillers in a resulting structure such as paper, made from these fibers. In addition, if the granular polymer materials are thermoplastic, or constitute a hot melt adhesive, they may subsequently be heated to cause further binding of the fibers and structure in which the fibers are included.

Desiccants (drying agents) and sorbents may similarly be attached to fibers by the binder while still retaining a substantial amount of their functionality. Again, the fibers anchor these particles in place and in structures made of the fibers.

Bulking agents, that is particles having a relatively low density and high bulk, may be defined as follows: a particle with a density of less than twenty to twenty-five pounds per cubic foot and having voids therein. Most preferably the density of these particles is less than ten pounds per cubic foot. Specific examples would be styrene foam beads and polyvinyl dichloride microspheres. These particles may also be attached to fibers to enhance the bulk of these fibers. Fibers including these bulking agents, with foam particles being one specific example, would have excellent thermal insulating characteristics as well as excellent shock absorbing characteristics when used in packaging. Fibers with attached high bulk particulates would in general be useable in applications where high bulk is desired.

Friction altering particles may also be adhered to fibers by the binder. These particles may include lubricating materials such as graphite and PTFE (TEFLON TM PTFE) as a few specific examples. In addition, friction inducing materials, such as rubber particles, may be adhered to fibers by the binder. Structures of these fibers are useable in applications requiring lubrication or high levels of friction.

Surfactants in particulate form may be adhered to fibers by the binder for use in altering the characteristics of the fiber, for example increasing its wettability, when used in various processes.

Chitosan is yet another particle which may be attached to fibers. It is believed that chitosan may promote the healing of wounds. Therefore, adhering this material to fibers which are then included in a dressing for a wound or the like, would take advantage of this attribute of this material. In addition, chitosan is also soluable and useable as a binder. Given the film forming nature of a chitosan solution, it is also expected to substantially continuously coat the fibers and serve to bind particulate materials to the fiber.

Particles having pollutant filtering properties may also be attached to fibers. When incorporated in filter or other structures used in cleaning up particular pollutants, these particles would substantially be retained in the structures for delivery to the spill or the location where they are to be used. Particles of materials targeted for specific pollutants may be selected and used.

Indicator particles, such as water and other chemical indicators, may also be adhered to fibers by the binder. These indicators may be incorporated into absorbent structures, such as diapers, and used, for example, to indicate that the absorbent structure has become wet.

It is common for fibers to be incorporated into nonwoven fabrics. By attaching fabric softeners to these fibers, or in other webs, enhanced softness of the resulting fiber structure is achieved.

In addition, particles with antistatic properties may be adhered to fibers by the binder and thereafter incorporated into structures. For example, these fibers may be included in floor mats useable in reducing static electricity around sensitive electronic equipment and systems.

In addition, more than one type of particle may be bound to the fibers if the functional characteristics of more than one particulate material are desired. Also, particulate containing fibers may be included in a wide variety of structures, including absorbent structures, a few examples of which are set forth below in connection with Example 14. Fibers with adhered particulates may be blended with other fibers and materials in making these structures.

Again, preferably the binders are of a polymeric heat bondable type (for example thermoset or thermoplastic binders) so that they may be subsequently heat bonded, with or without other fibers, in manufacturing a product. However, inorganic materials, such as liquid sodium silicate, in an amount sufficient to provide a substantially continuous coating of the fibers may also be used to adhere particles to the fibers. Although such materials are not used in binding fibers together during subsequent processing, they are capable of binding particles to the fibers and thus in this sense can be called binders. In addition, these materials, when coated on the fibers, add characteristics to the fibers. For example, silicon dioxide increases the wettability of the fibers.

EXAMPLE 5

This example is like example 4, except that super absorbent particles are adhered to the fibers by the binder material. These super absorbent particles are well known in the art. Various amounts of super absorbent particles have been successfully adhered to the fibers, including from fifteen to fifty percent of the dry weight of the resultant fiber, binder and additive combination. Lower percentages are also possible as are higher percentages. A specific example of super absorbent particulate material is SANWET IM-1000 superabsorbent particles, available from Celanese Corporation.

In one more specific example of the method, rather than stopping the fibers to permit addition of the particulate material, super absorbent particles were fed into the air stream containing the entrained fibers immediately following the binder application zone. The resultant material had fiber bonded to the super absorbent particles so as to contain the super absorbent particles in the resultant fluff. The fibers which were not attached to the particles were substantially unbonded to one another. The dried fluff was then air laid into a web and thermobonded. The web was tested for absorbency and found to be equivalent to an unbonded product, but with virtually 100 percent containment of the super absorbent particles. In addition, the containment of the super absorbent particles within the fibers prior to thermobonding was also excellent. Also, a very uniform distribution of super absorbent particles was present in the resulting web and enhanced the water absorbing characteristics of the web. Consequently, the fibers can be stored and transported for subsequent use in products without significant loss or migration of super absorbent particles.

Starch has also been used as a binder for fibers and to attach particulate material to fibers. At the present time, starch is a relatively inexpensive material for use as a binder in comparison to latex binders, such as polyvinyl acetate-based latexes. Starch is also a naturally hydrophilic material with the same general chemical formula as cellulose, which makes starch especially suitable for aqueous-based absorbent structures.

One suitable starch binder is of the type used on paper machine size presses, such as CHARGEMASTER R465 starch from Grain Processing Corp. of Muscatine, Iowa. In a specific example, this starch was first ground in a mortar and pestle and then slurried in water at a concentration of 20 percent by weight. Unlike the typical paper making application, the starch was not cooked. Starch was applied to NB316 wood pulp fibers at respective 15 and 30 percent starch loading levels (the percentages being by weight of starch to the combined weight of the starch and fiber). This loading was achieved in the same manner as Example 1 above. The resulting starch treated fiber had a dry bulk of 42.8 cc/g (for the 15 percent starch loaded fibers) and 42.7 cc/g (for the 30 percent starch loaded fibers). This compares with an average bulk of 53.3 cc/g for untreated NB316 fiber. The liquid absorbent capacity for these products was 11.8 g/g for a 15 percent starch loaded fiber, 12.2 g/g for a 30 percent starch loaded fiber, and 13.6 g/g for untreated NB316 fibers. In determining absorbent capacity, a 0.1 gram sample of these fibers formed into an airlaid pad was placed on a screen with the screen then being placed in contact with synthetic urine for thirty minutes. The pad was weighted with a 2.5 kPa load during the test. The liquid absorbent capacity is the difference between the wet and dry weights of the sample divided by the dry weight of the sample. The absorbency time was 5.6 seconds for 15 percent starch loaded fiber, 6.2 seconds for 30 percent starch loaded fiber and 4.1 seconds for NB316 wood pulp.

The absorbency time is obtained by airlaying a 4.0 gram sample of fibers under a low vacuum of about four inches of water into an unbonded cylindrical pad in a one and one-half inch diameter tube with a screen at the bottom. A 2.5 kPa load is applied to the upper surface of the pad using a plunger and water is brought into contact with the screen at the bottom of the tube. The absorbency time is the time required for the water to penetrate from the bottom to the top of the pad. Thus, although starch coated fiber showed some decrease in dry bulk, overall capacity, and absorbency time, a wettable fiber was still produced using this biodegradable binder.

The capacity of the starch to bond super absorbent (SAP) particles to the fibers has also been investigated. In particular, the circulation of fibers wetted with starch in the manner of Example 1 above was stopped to add super absorbent particles to the fibers. In particular, 1M-1000 super absorbent particles from Celanese Corp. was added to the fibers. Recirculation of the fibers was then commenced to mix the super absorbent particles with the fibers. Fibers with starch at the previously mentioned loading levels of 15 and 30 percent were subjected to super absorbent particle loading respectively at about 50 and 25 percent (the percent being based on the weight of super absorbent particles to the combined weight of fibers, binder and super absorbent particles). The tested 15 percent starch loaded fibers actually had a measured SAP content of 47.9 percent. When pressed in a pad former, the SAP content was measured at 46.5 percent, indicating very little SAP loss during formation of the pads. These pads were formed in the following manner: Small portions (0.3–0.7 grams) of the fluff/SAP material are drawn, by suction, through a mixing device consisting of two shafts with perpendicularly arranged pins rotating counter to each other. This mixing device is connected to the suction by a six-inch diameter tube that rests on a forming screen covering the inlet of the suction device. After the fluff/SAP material has passed through the mixing device, it is drawn down onto the forming screen by the suction and, to a lesser extent, gravity. The mixing device/forming screen is continuously fed the fluff/SAP mixture until a pad of the desired weight is obtained. In addition, when a sample of these fibers were run through a sonic fractionator and a +5 sieve fraction tested for SAP content, the measured SAP content was 48.0 percent, again confirming the retention of SAP on the fibers when the fibers were stressed by passage through a sonic fractionator. The sonic fractionator and sieve testing was performed as follows: Five gram aliquots of the fluff/SAP mixture are broken into small portions (0.1–0.4 grams) and distributed evenly over a five-mesh screen. The five-mesh screen is placed over a tower of sieves (screens) with meshes of eight, twelve, sixty and two-hundred. A speaker oscillating at approximately 200 Hz is placed over the sieve tower and allowed to vibrate for six minutes. Successive sieves are then checked for the amounts of fluff, SAP, and fluff/SAP composite trapped in each one. Three replicates are done on each sample. In comparison, 30 percent starch loaded had a measured SAP content of 27.0 percent when pressed in a pad former, the measured SAP content dropped to 26.5 percent, again indicating that virtually all of the SAP was retained the fibers during pad formation. In addition, when run through a fractionator and a +5 sieve fraction was tested, the measured SAP content was 27.6 percent (within experimental error of the 27 percent original level), again confirming the retention of the SAP on the fibers during this test.

Unlike the situation when thermoplastic, thermos and wax binders were used, SEM micrographs of starch treated fibers displayed granules or lumps of starch on the fiber and not the smooth coherent sheath or film of binder seen with these other binders. Nevertheless, starch has proven to be a very effective binder in applying SAP particles to fibers.

EXAMPLE 6

In this example, two solutions were prepared containing water insoluble dyes or colorants, Morton Purple KI and Hytherm Black B. Each solution contained fifty percent acetone and fifty percent of one of the dyes. Each dye solution was added to a forty-five percent solids latex binder, namely SYNTHEMUL 40-800, so that the dye equaled five percent of the latex solids by weight. The dye-containing binders were then applied to entrained NB-316 cellulose fibers in a Waring blender. The fibers were pigmented by the dye and had a substantially continuous binder and dye coating. The fibers were also substantially unbonded. The latex and dye mixture was thirty percent of the combined dry weight of the binder, dye and fibers. These pigmented fibers were allowed to dry and then used to prepare a one percent suspension in water. After one hour, this suspension was filtered through a Buchner funnel. Examination revealed that the residues were pigmented fibers and the filtrates were clear water. If these pigmented fibers are used in a wet laid paper making process, the dye would be substantially retained on the fiber and would not leach into water used in the process. Also, dye or colorant would not leach from towels and other products made from these fibers when these products are used, for example, to wipe up liquids. Consequently, colored paper board may be manufactured using these fibers without requiring the addition of dye to water. Once dye is added to water in paper making equipment, it is difficult to remove the dye from the equipment in order to, for example, change colors of paper. This problem can be avoided by incorporating the dye or colorant in the binder. Particulate pigment or dye materials may also be mixed with the binder and sprayed onto the fiber to form pigmented fiber. For example, particles of $TiO_2$ may be applied in this manner.

EXAMPLE 7

In accordance with this example, the binder can be mixed with a blowing agent, such as Azodicarbonamid, and applied to the entrained fibers. When the fibers are subsequently heated, nitrogen, carbon dioxide, and/or other gases would be released to produce a foamed coating of the fibers. These foam coated fibers can then be used in manufacturing, such as in the manufacturing of insulated paper board.

EXAMPLE 8

In accordance with this example, the binder may be a hydrophobic resin or latex material with hydrophobic particles; the binder may be of a hydrophobic material with the particles hydrophilic; the binder may be a hydrophilic material with hydrophobic particles; or the binder may be a hydrophilic material with hydrophilic particles. A fugitive surfactant is typically used when water based binders are used and the fibers or particles are hydrophobic.

Thus, a binder such as PRIMACOR binder may be used with hexanol as a surfactant as explained in connection with example 1 as a hydrophobic binder. As another example, PMDI may be used as a hydrophobic binder (see example 3). While PRIMACOR and PMDI binders have a tendency to absorb oil to a limited extent, they are not optimum oil absorbing materials. By attaching polynorbornene particles to the fibers, fibers having an enhanced capacity for oil absorption may be produced as the polynorbornene in effect acts like a super absorbent for oil.

An example of a hydrophobic binder with a hydrophilic particulate material would be fibers coated with PRIMACOR or PMDI binders with super absorbent particles adhered to the fibers by the binder. For example, fibers containing a twenty percent PRIMACOR binder, forty percent by weight super absorbent particles, and forty percent by weight fiber, have been produced. These percentages are of the total dry weight of the binder, fiber and additive combination.

An example of a hydrophilic binder with hydrophobic particles would be SYNTHEMUL 40-800 as a binder and polynorbornene as the particles.

Finally, an example of a hydrophilic binder with hydrophilic particles is SYNTHEMUL 40-800 as a binder and super absorbent particles as the hydrophilic material.

EXAMPLE 9

The binder may also be comprised of a thermoplastic binder material together with plasticizer particles or liquid which cause the polymer to soften when subjected to heat. A specific example of a liquid plasticizer is dioctyl phthalate. A specific example of a particulate plasticizer is sold under the brand name "SANTOWAX" plasticizer from Monsanto, Inc.

EXAMPLE 10

In accordance with this example, the fibers may be coated with plural binder materials. For example, the first binder material may be a thermoset binder material, such as phenolic resin, which can be applied to the fibers to increase their strength and rigidity. CASCOPHEN WC04 binder is an example of such a resin. This binder can be applied using the apparatus of FIGS. 1, 5 or 6 in accordance with the method of the invention. Following the application of the first binder, a second thermoplastic binder, such as PRIMACOR binder, can be applied to the fibers. This second coating can be used to bond particulate materials to the fibers that would not satisfactorily bond to a thermoset coating. During subsequent use of the fibers, they may be heated to the hot tack temperature of the outer binder coating for purposes of heat fusing the fibers. However, because the thermoset coating withstands higher temperatures, its integrity as a fiber and contribution to the strength of the bicomponent fiber remains. Thus, fibers having plural desired characteristics, such as a water repellant undercoating and a highly bondable outer coating, can be produced, with or without adhered particulate materials.

KRATON binder, a styrene butadiene block copolymer, available from Shell Chemical Corporation is an example of another hydrophobic and oleophilic binder material. This binder material does not form very strong bonds with uncoated fibers. Therefore, a highly bondable first coating, such as of PRIMACOR binder may be applied to continuously coat the fibers. KRATON binder in a lesser amount may then be applied to only partially coat the fibers. The exposed PRIMACOR binder coated areas then enhance the bondability of these fibers.

EXAMPLE 11

This example demonstrates the applicability of the process to cellulose fibers and fiber bundle material. Specifically, 1111 grams of a mechanically fiberized wood (ten percent moisture) were placed in a recirculating conduit 24 with an in-line blower. The blower was turned on and the wood fibers became air entrained. 952 grams of Reichhold's SYNTHEMUL 40-800 binder (fifty-five percent moisture) were sprayed onto the fiber through a port in the conduit. After addition of the latex, the material was shunted out of the loop 24, collected in a cyclone 60 and spread on a bench to air dry. Subsequent examination under a scanning electron microscope showed individual fibers and individual fiber bundles enclosed in a latex sheath with substantially no fiber to fiber, fiber to fiber bundle, or fiber bundle to fiber bundle agglomeration due to latex bonding.

EXAMPLE 12

This example demonstrates the enhanced oil absorbency characteristics of binder coated fibers with another type of attached oil absorbing particulate materials, in this case a hydrophobic fumed silica material.

Specifically, 107 grams of southern bleached kraft (NB316, seven percent moisture) were placed in a recirculating duct including a fan or blower. The fan was turned on and the fluff became air entrained. Seventy-nine and six tenths grams of binder, in this case, AF4530 latex binder from Air Products, Inc. of Allentown, Pa. were sprayed onto the fluff through a port in the recirculating duct. After the latex was sprayed, the fan was turned off and ten grams of a hydrophobic fumed silica particulate material, in this case AEROSIL R812 from Degussa, Inc. of Richfield Park, N.J. was added to the fibers. The fan was then restarted and the mixture circulated for one minute to ensure complete mixing. This yielded a mixture that was approximately thirty percent by weight binder, seven percent by weight silica, and sixty-three percent by weight fiber. The mixture was shunted into an air permeable nylon bag, collected and spread out on a bench overnight to air dry. A sample was then taken for testing for hydrophobicity and oleophilicity. The sample floated on water for one month (after which the test was stopped). When the material was placed in a layer of diesel oil (No. 3 diesel oil) over a layer of water, the material absorbed approximately 15 times its weight of the diesel oil almost instantaneously. In addition, the material remained in the oil layer overnight (after which the test was stopped). Therefore, surprisingly a hydrophilic material, namely wood pulp, when treated in this manner, floated for a substantial period of time and also was rendered highly oil absorbent. This fiber, as well as absorbent structures of this material, is therefore a candidate for spreading on oil spills and the like, in particular oil spills in bodies of water, for environmental clean-up purposes.

To further confirm the versatility of this example, it was repeated utilizing 107 grams of reground mixed waste (seven percent moisture) paper, with this material being placed in a recirculating duct, including a fan or blower. Following air entrainment of the fiber, seventy-nine and six-tenths grams of AEROSIL AF4530 latex binder was applied as explained previously. In this case, the fan was turned off and 1.1 grams of Degussa's AEROSIL R812 was added with the fan being restarted and the mixture circulated for one minute for mixing purposes. The resulting mixture was approximately 30 percent by weight binder, 0.7 percent by weight silica, and 69.3 percent by weight fiber. The mixture was shunted into an air permeable nylon bag, collected and spread out on a bench overnight to air dry. A sample was then taken, heated to 170° C. for one minute and then tested for hydrophobicity and oleophilicity. Again, the sample floated on water for one month (after which the test was stopped) and, in a separate test, the fibrous material absorbed approximately 15 times its weight of No. 3 diesel oil almost instantaneously. When the material was tested in a layer of diesel over a layer of water, the material remained in the oil layer overnight (after which the test was stopped).

The test of the previous paragraph was also repeated except that ten and eight-tenths grams of sodium octaborate, a fire retardant, dissolved in thirty grams of deionized water was sprayed onto the fluff prior to the application of the binder. Thereafter, the binder and AEROSIL R812 was added to yield a mixture which was approximately 30 percent by weight binder, 0.7 percent by weight silica, 7 percent by weight sodium octaborate, and 62.3 percent by weight fiber. The sample was tested as described in the preceding paragraph, with the results being the same as s forth in the preceding paragraph.

EXAMPLE 13

This example illustrates the use of wax, and in particular a wax emulsion, as a suitable binder material for fiber. In this case, 170 grams of southern bleached kraft (NB316, 7 percent moisture) were placed in a recirculating duct including a fan or blower. The fan was turned on and the fluff became air entrained. 857 grams of wax emulsion (wax emulsion WB-1971 from H. B. Fuller Company of Vadnais Heights, Minn.) were sprayed onto the entrained fluff. The mixture was shunted into an air permeable nylon bag, collected and spread out on a bench overnight to air dry. A sample was then taken and tested for hydrophobicity and oleophilicity. The sample floated on water overnight (after which the test was stopped).

Substantially all (about 95 percent) of the fibers treated in this manner had a substantially continuous coating of the wax binder. The wax binder would also be suitable for attaching particulate materials to the fibers.

EXAMPLE 14

Example 14 describes the attachment of antimicrobial particles to fibers. In addition, this example ss forth a number of absorbent structures which may be formed from fibers with attached particulate materials, such as antimicrobial particles. It should be noted that these exemplary absorbent structures are simply examples as the fibers may be incorporated into structures, including rigid structures and nonabsorbent structures, of virtually any shape or form. In addition, although this example focuses on the use of antimicrobial particles, other particles attached to fibers may be similarly included in these structures or other structures, in addition to, or instead of the antimicrobial particles.

Figure 6:
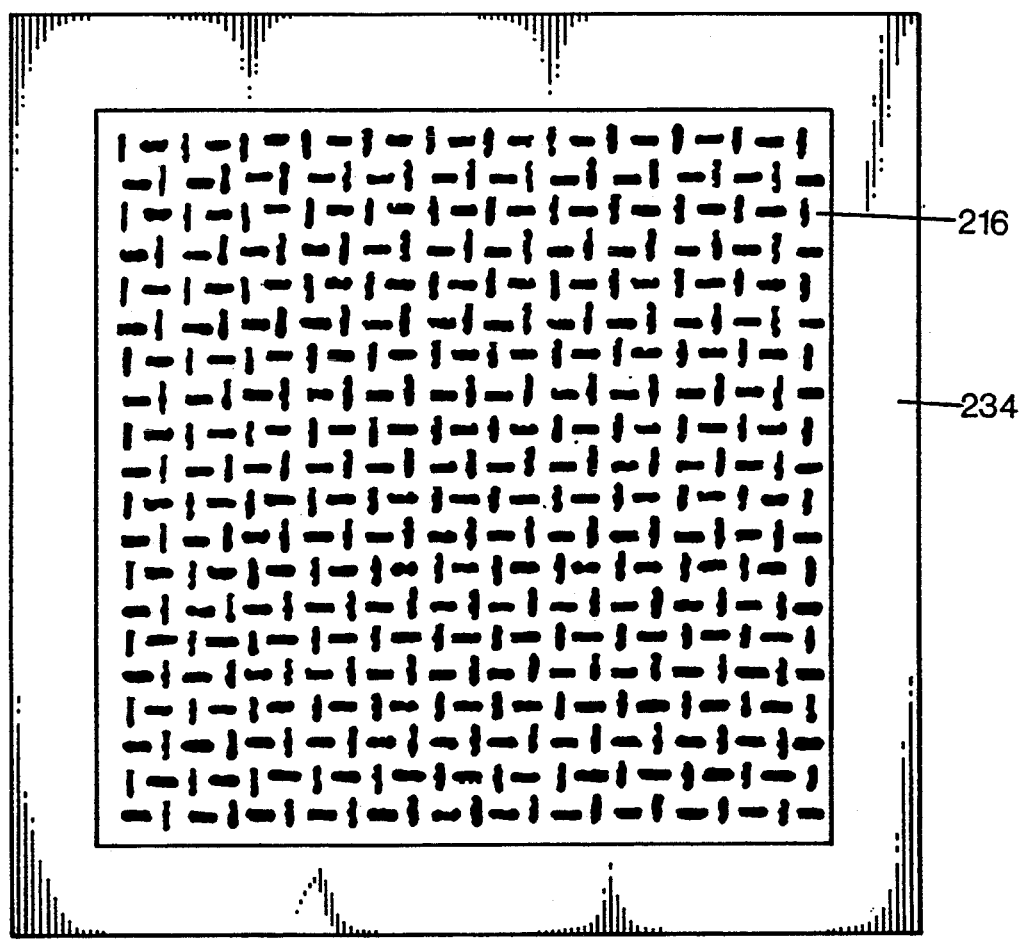
FIG. 6 is a top plan view of an absorbent structure in the form of an absorbent pad formed of fibers of the invention, which may include particulates such as antimicrobial particles, attached to the fibers.

With reference to FIG. 6, an absorbent insert 216 is illustrated and comprised of fibers of the present invention including a binder material coating. The fibers may be at least partially coated with a binder material while most preferably the binder material may substantially continuously coat the fibers. The fibers, which are preferably discontinuous fibers of the type described in greater detail above, can be bound together by the binder material to form a substantially bonded pad. By substantially bonded, it is meant that the majority, and preferably all, of the fibers are bound together at the contact points of the fibers. The binder material, as previously explained may take a number of forms. However, it is preferable for the binder material to be of a heat bondable type, so that the pad may be bonded or fused together by heating the binder material to its softening point. The insert may also be of loose unbonded fibers which may be enclosed within a case. However, bonded fibers are preferred as they do not tend to bunch up.

A substantially unbonded pad may also be formed. This type of pad consists of fibers which include a binder material which is used to adhere antimicrobial particles to the fibers. The pad may also include super absorbent fibers and/or other particles which are also adhered to the fibers by the binder material. The fibers are not bound together at their contact points and the pad remains unbonded.

One specifically preferred binder material for attaching antimicrobial particles to fibers is PN 3666H available from H. B. Fuller Company and applied to the fibers in an amount which is thirty-three percent by weight to the weight of the fibers.

An antimicrobial is a substance which inhibits the growth of microorganisms by either destroying them or suppressing their growth. As defined herein, the term antimicrobial includes substances which are antiprotozoan, antiviral, antibacterial, antirickettsial and antimycotic (including antifungal and antiyeast). The absorbent pad 216 may include at least two different antimicrobials. A variety of combinations of antimicrobials may be used to destroy or suppress different types of organisms, making the package suitable for a variety of specialized uses. The different antimicrobials in particulate form may be adhered to the common fibers. In the alternative, each different type of antimicrobial may be adhered separately to different fibers.

The antimicrobial particles are adhered to the fibers by the binder material. As used in this specification, a particle is defined as a dense, solid material having a length to width ratio of no more than six to ten. Alternatively, the antimicrobial (and for that matter other particles) may be in the form of a crystalline needle or a fiber having a higher length to width ratio and still fall within the definition of a particle. The antimicrobial particles will inhibit the microbes present in the spilled liquid which is absorbed by the pad. A wide variety of antimicrobial agents may be used depending upon the type of specimen to be transported. Quaternary ammonium salts, parachlorometa xylenol, dichlorophen, chlorhexidine diacetate, chlorhexidine, chloramphenicol, nitrofurazone, miconazole nitrate (1-[2,4-dichloro-B-(2,4-dichlorobenzyloxy) phenethyl] imidazole), clotrimazole ([1-(o-cholor-α,αdiphenylbenzyl) imidazole]), and benzoyl peroxide are a few examples of known suitable antimicrobials. These materials are commercially available in particulate forms. An effective amount of antimicrobial would be microbial and target dependent and can be determined from the literature describing such products or by culture testing, for example. In cases where the fibers are to be heat bonded, antimicrobials are selected which are not degraded by the heat being applied during bonding so as to be rendered ineffective in inhibiting microorganisms. Information on heat degradation of antimicrobials is typically available in the literature (e.g. the Merck Index) or can be readily determined by heat and culture testing. A particularly effective amount of antimicrobial may be within the range of about 0.01 percent to about 5 percent by weight of the weight of a pad.

Figure 7:
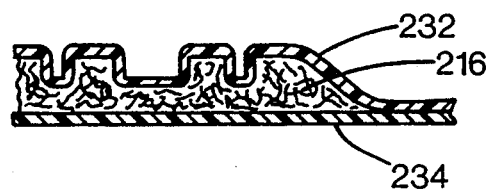
FIG. 7 represents a partial sectional view of the pad of FIG. 6.

As best shown in FIG. 7, the absorbent insert 216 may have a cover she 232 and a backing she 234. The fibers of pad 216 thus comprise a core between the cover she 232 and the backing she 234. Cover she 232 is preferably made of any suitable material, including nonwoven materials, which will readily permit the passage of liquid through the cover she to the absorbent pad 216. The following list of liquid permeable materials is provided by way of example only: nonwoven sheets of rayon, nylon fibers, polyester fibers, polypropylene fibers and blends thereof. A specifically preferred cover sheet material is a 70% rayon/30% polyester blend having a basis weight of 21.5 grams/m$^2$, available from the Scott Paper Company.

The backing sheet 234 may be, but is not necessarily, made of a liquid impermeable material, including but not limited to, films of polyethylene, polypropylene and polyester and blends thereof along with nylon and polyvinyl chloride films. A specifically preferred backing sheet material is a 0.004 inch polyethylene film from Dow Chemical Company.

It is preferable to have the cover sheet 232 and the backing sheet 234 of a heat bondable material. When the fibers of pad 216 are heated in a thermobonder to bond the fibers, the heat bondable cover sheet and backing will likewise be heat bonded to the core fibers and may also be heat bonded at the periphery of the pad. The periphery of the pad refers to the intersection of the cover sheet and backing sheet at a point off of or apart from the fiber core of the pad. Alternatively, cover sheet 232 and backing sheet 234 may be adhesively bonded together at the periphery of pad 16. Also, the fibers may be unbonded and simply placed between the cover sheet 232 and backing sheet 234, but a bonded fiber core is most preferred as it adds to the strength and integrity of the pad.

Thermobonding of the binder material will at times partially, and sometimes totally, encapsulate the antimicrobial particles. This encapsulation is expected to provide a time release of the antimicrobial. Some antimicrobials are able to slowly diffuse through the binder material and thus will function even if totally encapsulated although total encapsulation would be expected to slow down the release of the antimicrobial to the diffusion rate through the binder material. Antimicrobials have varying solubilities in water. The solubility of particulate antimicrobials is typically known or readily determinable. Thus, by selecting antimicrobials of different solubilities, a time release of the antimicrobial can be achieved. Water is a major component of most body fluids. When partially encapsulated, the antimicrobial will diffuse into water at a rate which is related to the diffusion rate of the antimicrobial into water and the exposed (unencapsulated) surface area of the antimicrobial. Again, a time release of the antimicrobial can be achieved.

Figure 8:
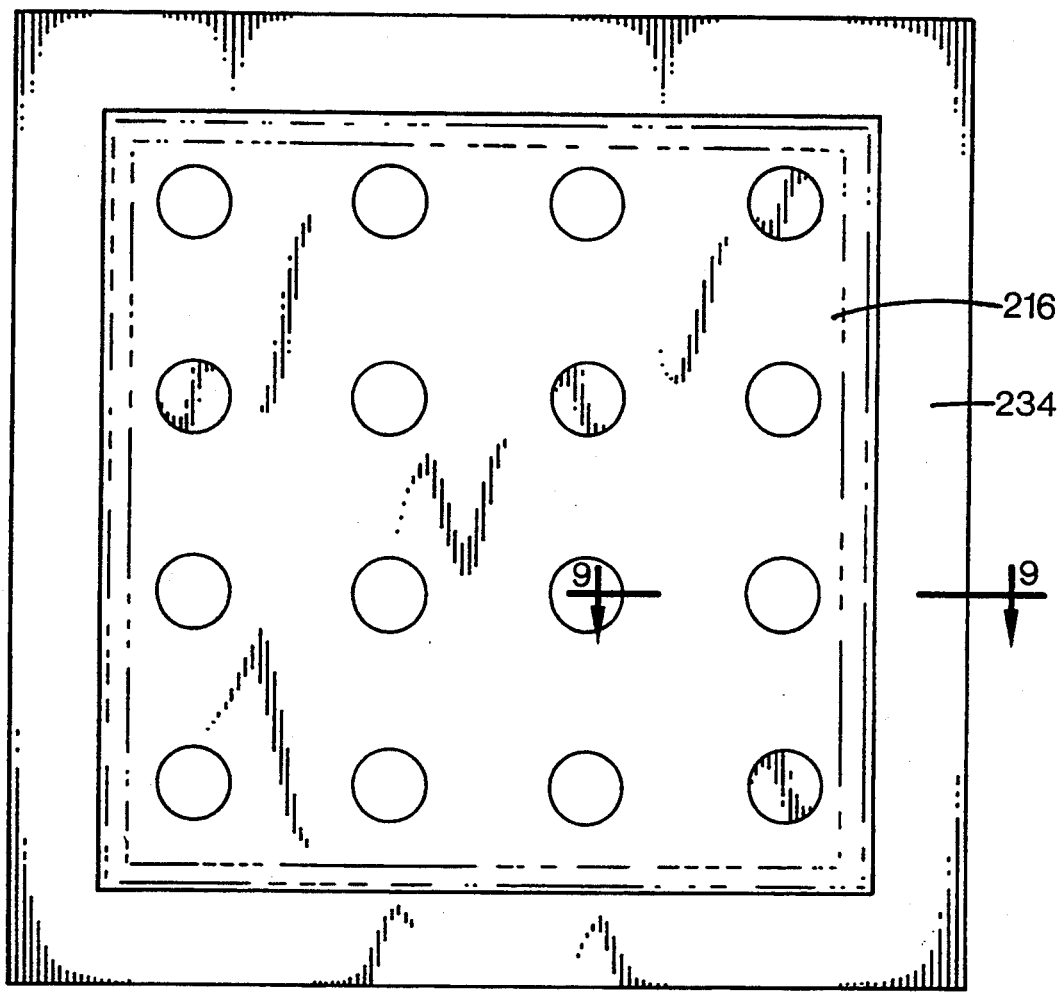
FIG. 8 represents a top plan view of an alternative absorbent pad structure formed in accordance with the present invention.
Figure 9:
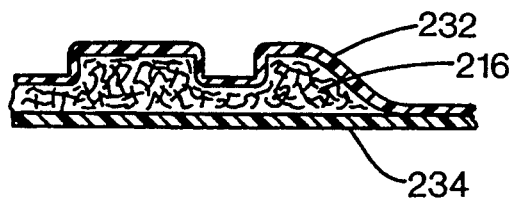
FIG. 9 represents a partial sectional view of the pad of FIG. 8, taken along line 9—9 of FIG. 8.

FIGS. 6–9 illustrate examples of different types of absorbent pad structures which may be formed from fibers of the present invention, whether or not they are blended with other fibers. FIGS. 6 and 7 represent an absorbent pad having a heat embossed screen pattern. FIGS. 8 and 9 represent an alternative absorbent pad having a dot matrix pattern. Pads having no pattern may also be used and are presently preferred (see for example pad 216 of FIG. 16). A pad having a cover sheet and a backing sheet may be formed, for example, by placing a square bonded fiber piece cut from the sheet onto a corresponding precut backing sheet. A corresponding precut cover sheet is placed over top of the fiber on the backing sheet. This assembly may then be heat pressed or adhesively bonded with or without a pattern.

Preferably, in embodiments of the invention wherein a pad is enclosed between cover sheets and wherein the pad includes super absorbent particles, an expansion region is provided to accommodate swelling of the pad due to the fluid absorbed by the super absorbent particles. For example, with reference to FIG. 3, the edges of the pad may be surrounded by an unbonded region of the cover sheets between the edges of the pad and bonded periphery of the cover sheets. The pad in this case can expand into the space between the unbonded cover sheets without rupturing the bonded periphery of the cover sheets.

As a specific example which illustrates the effectiveness of antimicrobial particles attached to fibers; one hundred seven grams of Southern bleached kraft (NB 316,7% moisture) were placed in a recirculating duct including a fan or blower. The fan was turned on and the fluff became air entrained. Ninety-nine grams of H. B. Fuller's PN 3666H latex binder were sprayed onto the fluff through a port in the duct. After the latex was sprayed, the fan was stopped and fifteen and one half grams of particulate antimicrobial was sprinkled over the damp fluff. Five different batches of fluff were prepared, each with fifteen and one-half grams of a different antimicrobial particle, as listed below. The fan was restarted and the mixture circulated for one minute to ensure complete mixing. The particulate antimicrobials were adhered to the fibers by the latex binder material. The mixture was then shunted into an air permeable nylon bag, collected and spread out on a bench overnight to dry. Once dry, ten gram aliquots of the material were fed into a laboratory air-lay pad forming device and the resulting six inch diameter pads were pressed at a ram pressure of ten thousand psig with three millimeter shims for fifteen seconds. The pads were then placed in a 130° C. through air oven (thermobonder) for thirty seconds and then allowed to cool. Control pads were made in the same fashion with the exception that no antimicrobials were added to the mixture. Pads and unbonded antimicrobial particle containing fibers were then examined by SEM (Scanning Electron Microscope) and EDAX (Energy Dispersive Analysis by X-Ray) equipment to verify the presence of antimicrobials. Pads and unbonded fibrous material with adhered antimicrobial particles were also sent to a microbiological laboratory for efficacy testing.

The SEM evaluation revealed the presence of antimicrobials in both the unbonded fibers and thermobonded materials. In most cases however, the antimicrobials appeared somewhat embedded in the latex coating in the thermobonded examples. EDAX revealed the presence of the antimicrobial (e.g. chlorine for examples A-D and nitrogen in example E) in specific regions of thermobonded material and proved the presence of antimicrobials in these samples.

In a procedure for testing microbiological inhibition of the material, 0.65 grams of each of the tested materials was mixed in a sterile test tube with ten milliliters of inoculated saline. After a sample contact time of thirty minutes at room temperature, the saline solution was plated. Results are as follows:

| SAMPLE | ANTIMICROBIAL | SAMPLE | ANTIMICROBIAL |
|---|---|---|---|
| A | Dichlorophen | D | Chloramphenicol |
| B | Chlorhexidine diacetate | E | Nitrofurazone |
| C | Chlorhexidine | F | None |

| SAMPLE | SALMONELLA CFU's per ml* | % Reduction | STAPH. AUR. CFU's per ml* | % Reduction |
|---|---|---|---|---|
| A | 20 | 97.8 | 400 | 99.2 |
| B | 80 | 91.2 | 100 | 99.8 |
| C | <10 | >98.9 | <100 | >99.8 |
| D | 80 | 91.2 | <100 | >99.8 |
| E | 30 | 96.7 | 500 | 99.0 |
| F | 310 | 65.9 | 16,000 | 69.2 |
| A TB** | 90 | 90.1 | 2,900 | 94.4 |
| B TB | 290 | 68.1 | 24,000 | 53.8 |
| C TB | <10 | >98.9 | <100 | >99.8 |
| D TB | 60 | 93.4 | 4,200 | 91.9 |
| E TB | 50 | 94.5 | 50,000 | 3.8 |
| F TB | 430 | 52.7 | 26,000 | 50.0 |
| Saline control | 910 | | 40,000 | |

*Colony Forming Units per ml of inoculated saline.
**TB refers to thermobonded pad.

Therefore, the resulting antimicrobial particle containing fibers and pads proved effective in inhibiting microorganisms.

Pads manufactured as described above may be of any size (e.g. four feet by four feet) for use in absorbing bodily fluids, such as surgical pads.

Figure 10:
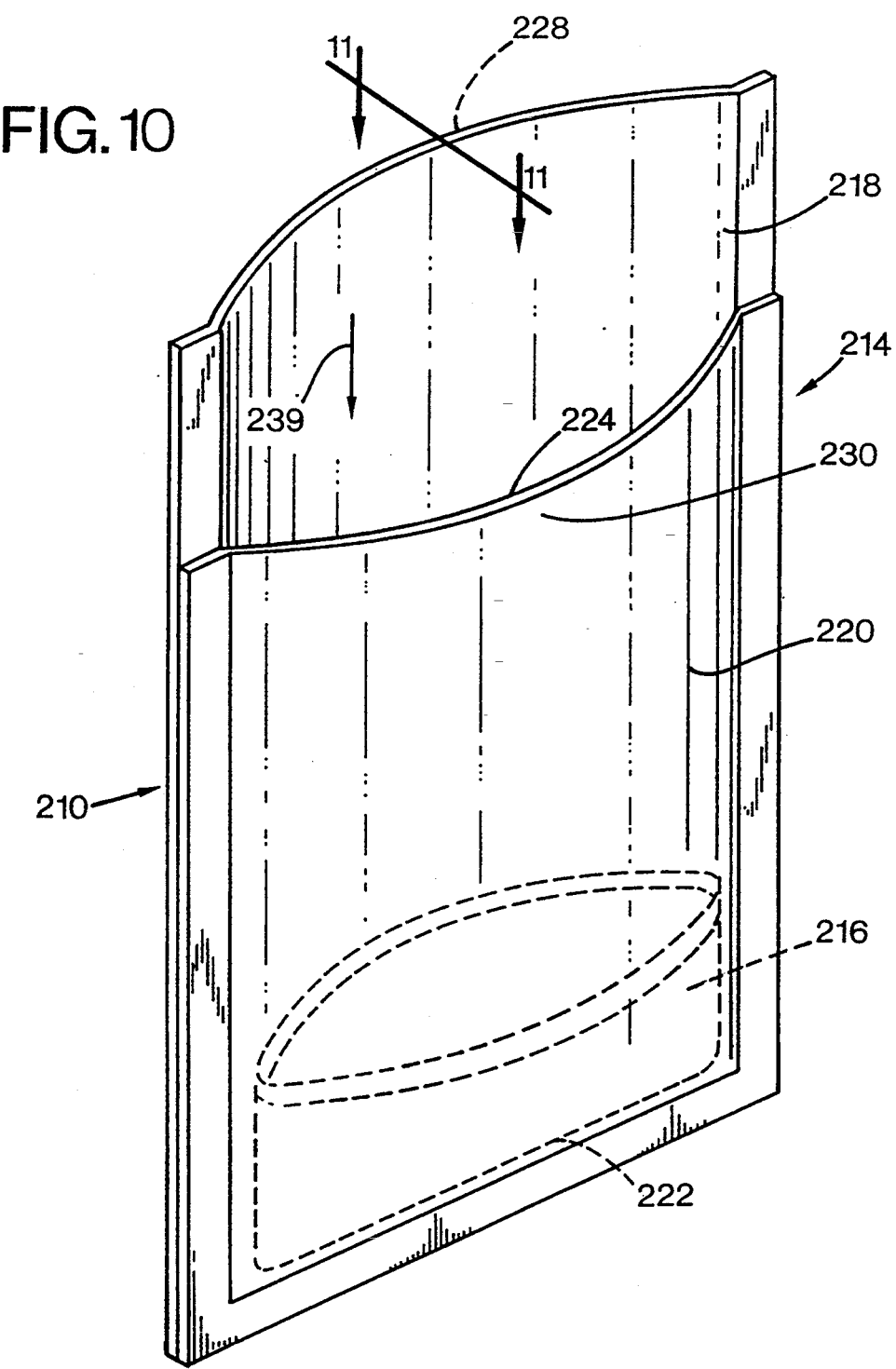
FIG. 10 represents a perspective view of a package incorporating an absorbent pad structure to further illustrate the diversity of structures in which fibers of the present invention are useable.
Figure 11:
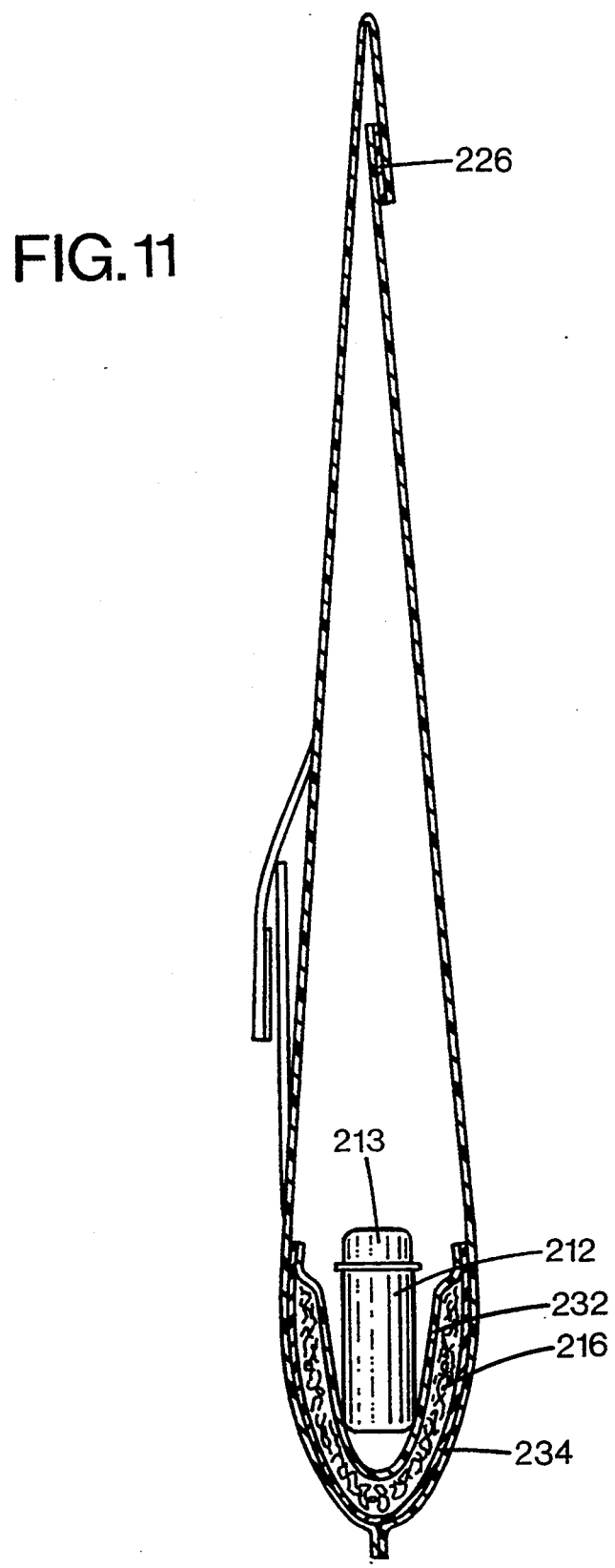
FIG. 11 represents a vertical sectional view taken along line 11—11 of FIG. 10.
Figure 12:
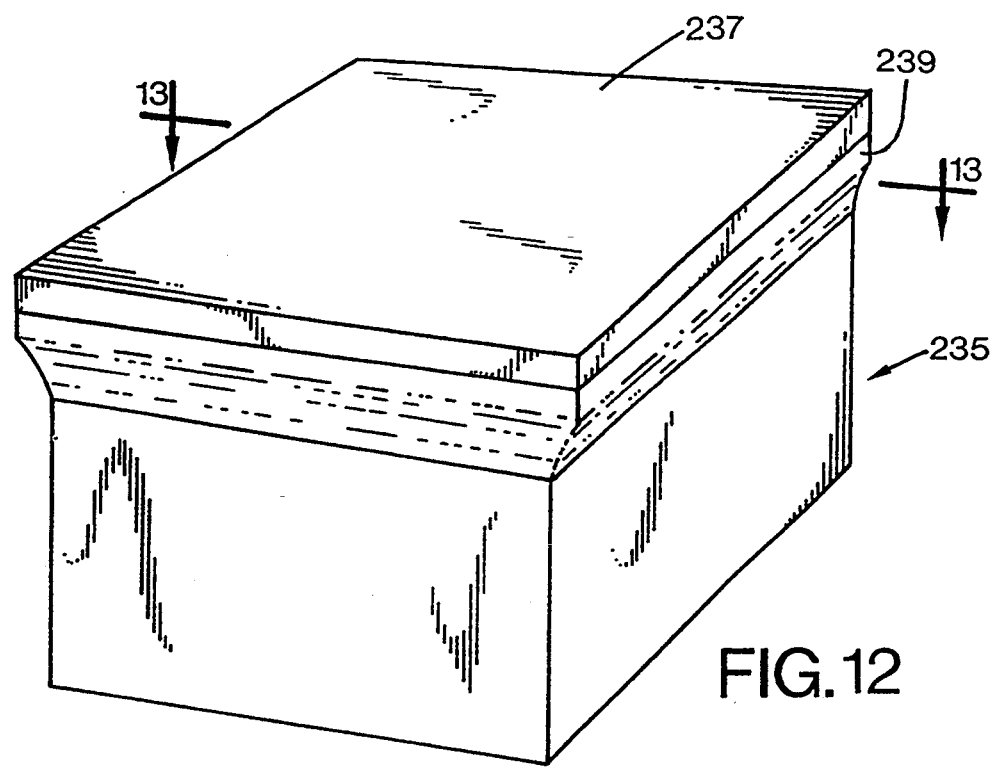
FIG. 12 illustrates a package which can incorporate or enclose fibers of the present invention.

The absorbent structures of fibers of the present invention and the fibers may be included in a wide variety of absorbent structure products. For example, as shown in FIGS. 10 and 11, a package 210 is provided for transporting liquid specimens such as body fluids or medical specimens. Package 210 includes a specimen container 212 (shown in FIG. 11), an enclosure 214, in the form of a bag and an absorbent insert 216. Specimen container 212 is typically conventional and may be of a form such as a vial, a test tube, or a bottle. Specimen container 212 has a removable lid 213.

Bag 214 is made of a liquid impermeable material so that any liquid which may spill from container 212 will be trapped and contained within bag 214. In the event of a spill of the contents of container 212, the likelihood of leakage or dripping of the liquid into the outside environment is substantially reduced. However, in the event bag 214 ruptures, liquid can still escape. Also, spilled liquid can exit from the opening leading to the interior of the bag if the bag is not totally sealed. Examples of suitable liquid impermeable bag forming materials include, but are not limited to, plastic films such as polyethylene, polypropylene, polyvinyl chloride, P and cellulose acetate. A specifically preferred material is a 0.004 mm thick film of polyethylene. It will be appreciated that bag 214 may be of any suitable shape or size without departing from the scope of the invention. These bags are also known in the art and have been used heretofore to transport medical specimen containers.

Bag 214 has an interior surface 218, a front exterior surface 220 and a back exterior surface 228. The absorbent insert 216 is positioned within the interior surface 218 of bag 214 substantially near a bottom surface 222 of the bag. Bag 214 may be formed in any conventional manner. An opening 224 is provided in bag 214. Opening 224 is configured to allow the placement of specimen container 212 within bag 214 and the subsequent removal of the container from the bag.

Bag 214 may also include a sealing means, one form of which is best shown in FIG. 11. For example, an adhesive tab 226 may be affixed to back exterior surface 228 of bag 214. It will be understood that any suitable sealing means may be used, including but not limited to, conventional "peel-back" adhesive tabs. Other mechanisms include mechanical clips or seals, heat sealing and other adhesive sealing techniques. The bag 214 may be sealed by affixing adhesive tab 226 to front exterior surface 220 at a point 230 substantially near the opening 224. Alternatively, adhesive tab 226 may be affixed to the interior surface 218 of the bag 214 and bag 214 may be sealed by affixing tab 226 to a point substantially near opening 224 of the front side 230 of front exterior surface 220.

Figure 13:
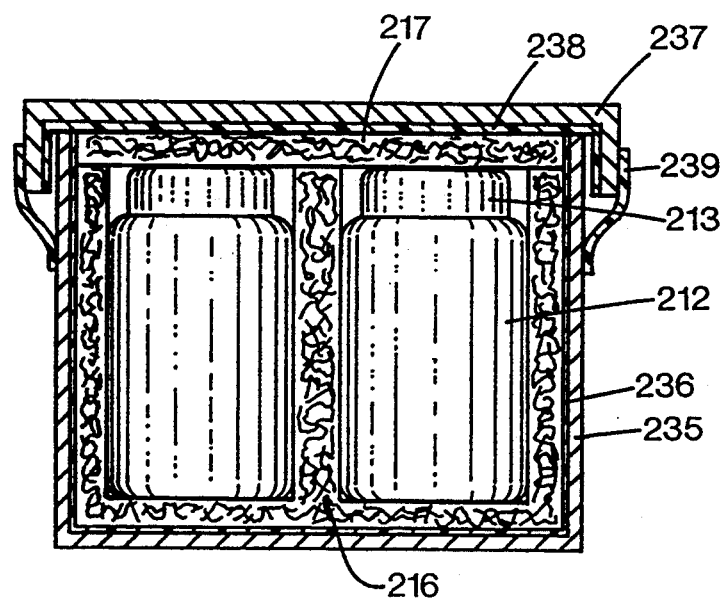
FIG. 13 is a sectional view of the package of FIG. 12 taken along line 13—13 of FIG. 12.
Figure 14:
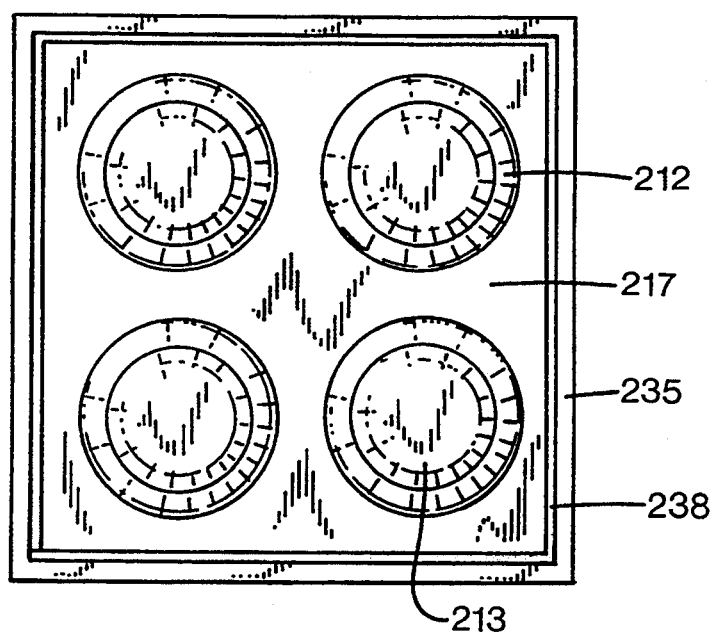
FIG. 14 is a top plan view of the embodiment of FIG. 12 with the lid of this container removed.
Figure 15:
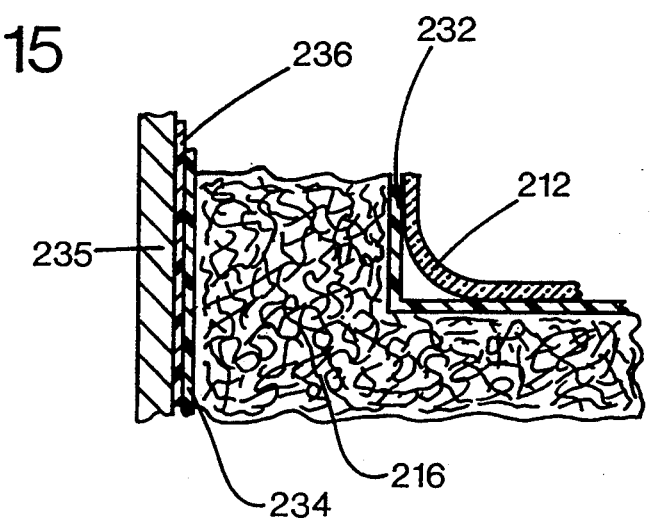
FIG. 15 is an exploded view of a portion of the package of FIG. 13.

The absorbent insert 216 may be in the form of a pad secured by conventional means to the interior surface 218 of bag 214. Pad 216 is provided to absorb any leakage of liquid from the specimen in specimen container 212. Insert pad 216 may be formed to define one specimen container receiving compartment, as shown in FIGS. 10 and 11. Pad 216 may also be formed to define plural specimen container receiving compartments, as shown in FIGS. 13 and 14.

An alternative structure of fibers of the present invention is shown in FIGS. 12-15 wherein the outer enclosure is made of a strong light weight somewhat rigid material, such as wood pulp paperboard. Larger enclosures are typically made of a corrugated fiberboard or solid fiberboard box material which meet the requirements of the specific application. For containers transported in vehicles, applicable governmental specifications should be met (e.g. Department of Transportation Uniform Freight Classification 6000H, rule 41, or other applicable governmental regulations). In this specific example, the enclosure is in the form of a box 235. It will be appreciated that the enclosure may be of any suitable shape or size. Box 235 includes a liquid impermeable interior surface 236 (FIGS. 13-15) to contain any leakage from the specimen containers.

The liquid interior surface 236 may be a liquid impermeable film. Examples of such films include, but are not limited to, plastic films such as polyethylene, polypropylene, polyvinyl chloride, and cellulose acetate. A specifically preferred example is about a 0.001 inch or less thick film of polyethylene secured by adhesive or extruded as in bleachboard to the interior surface of the box 235. Waxco and other box coatings may also be used for this purpose.

Box 235 includes a lid portion 237. Lid 237 includes an interior surface 238 which is also lined in the same manner with a liquid impermeable material. Lid 237 is capable of selectively closing an opening which communicates with the interior of box 235. The insert 216 also includes a lid portion 217 which is secured to the interior surface 238 of lid 237 of box 235. Lid 237 may be secured to box 235 using suitable sealing or latching means, such as mechanical fasteners or an adhesive plastic tape 239. Insert pad 216 may be molded and bonded or otherwise formed to define one or more, in this case four, specimen container receiving compartments. For example, the fibers of the insert may be formed around a screen mold and then thermobonded into the desired shape. Alternatively, the loose fibers may be laid to a constant depth and a ram or other suitable device may be used to press out specimen container receiving compartments. The fibers may also be thermobonded in sheet form with circles die cut out of each sheet. The individual sheets may be stacked one on top of the other to a sufficient height to form the insert with the cut outs forming the specimen container receiving compartments. Any number of specimen container receiving compartments may be formed within insert 16 in accordance with the present invention.

To form individual absorbent pads, smaller fiber pieces may be cut from the sheet, in a variety of suitable shapes and sizes. A pad formed in this manner may be of any basis weight, but preferably has a basis weight of from about 550 $g/m^2$ to about 750 $g/m^2$. The individual fiber pieces may be heat pressed or passed through an embossing roll to form densified bond regions, or compressed field locations, spaced from the periphery of the fiber pad. Different patterns may be pressed or embossed onto the pad depending upon the desired end use for the pad. It will be appreciated by those skilled in the art that each pattern imparts particular strength and texture qualities to the pad making the pad suitable for a variy of end uses. Preferably, the density of the compressed field locations is from about 0.7 g/cc to about 1.0 g/cc while the density of the core at locations spaced from the periphery at locations other than at the compressed field locations ranges from about 0.06 g/cc to about 0.12 g/cc. The pad is then pressed or molded into the desired shape, including the formation of the desired number of specimen container receiving compartments.

Particulates, such as antimicrobial particles, zeoiites, and other particles, may also be attached to bi-component fibers. One of the materials forming the bi-component material fibers may be a thermoplastic material or another material which will soften upon being heated to a specific temperature. Bi-component fibers, including thermoplastic bi-component fibers, are known in the art. Upon softening of one material of the fibers, the softened material is a binder and performs the function of the binder to bind fibers together in a structure and also to adhere particles, such as super-absorbent particles and/or antimicrobial particles and/or other particles thereto. The bi-component fibers are typically made of materials having heat softening or melting points. Typically, one of the components of the bi-component fibers is not melted or softened upon heating so as to maintain its fiber structure. One of the problems with bi-component fibers is that they tend to stick to one another and agglomerate when the bi-component material is heated to render it tacky for purposes of adhering particular materials. By passing these fibers through an attrition device, such as a hammermill, agglomeration can be eliminated to some extent. However, this would result in loosening some of the particulate material adhered thereto. Consequently, this approach, although representing another method of attaching particulate materials to a fiber having a binder, suffers from a disadvantage of a tendency to result in agglomerations of fibers which then are more difficult to process, for example by air laying, into absorbent structures. As another less preferred method, binders can simply be sprayed or otherwise applied to sheets of bulk fibers with the antimicrobial or other particles being disbursed onto or within the bulk fibers containing the binder. In this case, less uniform dispersion of binder and particles would result and very few, if any, fibers would have a substantially continuous coating of binder materials or even a substantial majority of their surface area coated with binder material.

With further reference to page 10, the insert or pad 216 may be secured, as by adhesive or otherwise, to the exterior surface of the bag 214. In this case, the bag 214 would comprise a support for the insert. In addition, the bag comprises a pouch into which a user's hand may be inserted, for example in the direction of arrow 239 shown in FIG. 10. It will be appreciated that the bag 214 may be of any suitable shape or size. In this alternative example, the absorbent structure 216, including particulate antimicrobial particles, would be positioned at the exterior of the bag 214 and, assuming the bag or pouch 214 is of a liquid impermeable material, the user's hand would be protected from liquid absorbed by the pad 216. In this case, the user may manipulate the bag or pouch 214 to contact the exposed pad 216 to a liquid spill and wipe the pad across the spill so that liquid is absorbed into the pad.

By making the pouch 214 of a flexible material, when the spill is absorbed, the user may reverse the pouch by turning it inside out as his or her hand is withdrawn. The pad 216 and the formerly exterior surface of the bag 214 are then positioned at the interior of the reversed pouch. Conversely, the former interior of the pouch is positioned to the exterior of the reversed pouch. In this case, the pad 216 is completely enclosed within the reversed pouch 214. By reversing the pouch, the chance of human contact with the pad or with any leakage therefrom is substantially reduced. Therefore, if for example the pad is used to clean up toxic or medical waste, for example blood or other bodily fluids or chemicals, the user is protected. The pouch 214 may include a sealing mechanism, such as previously described, positioned for use in selectively sealing the pouch 214 following use. Tapes, mechanical fasteners including clips, and heat sealing are examples of sealing approaches.

Figure 16:
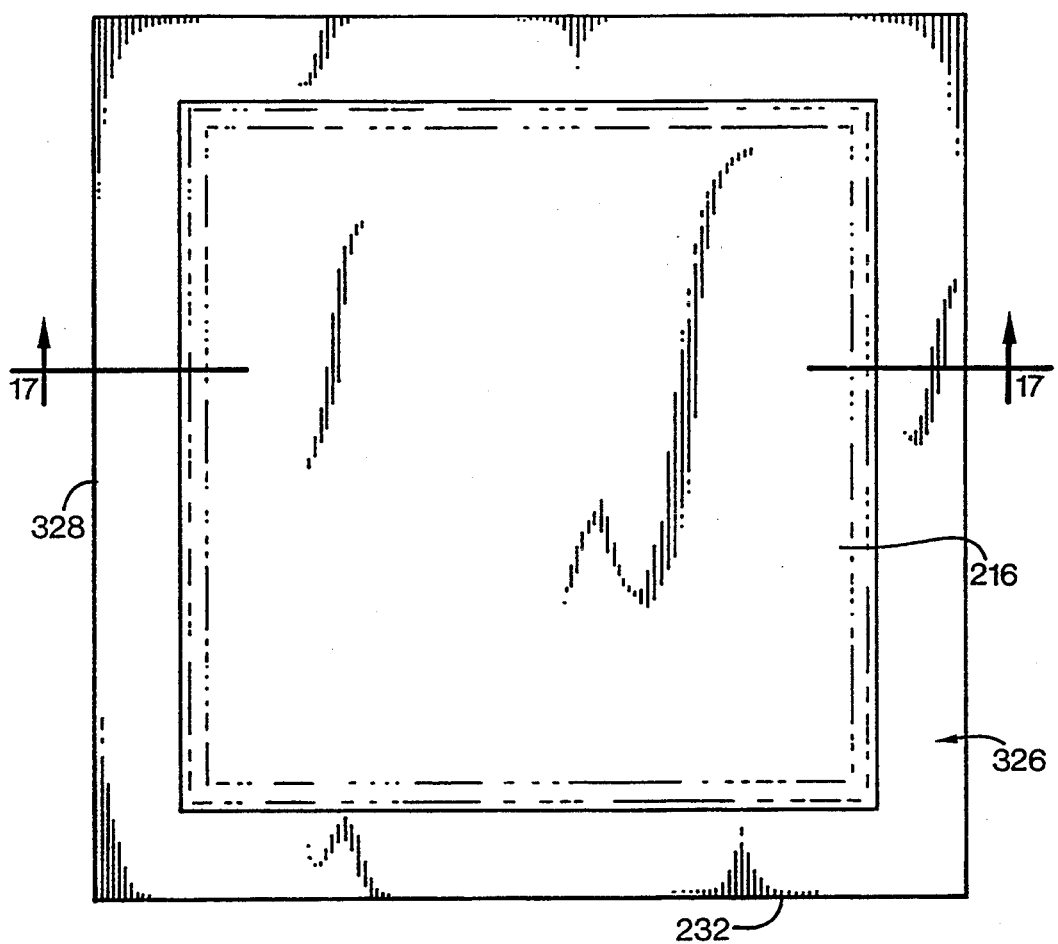
FIG. 16 represents a top plan view of yet another type of absorbent pad formed with fibers of the present invention.
Figure 17:
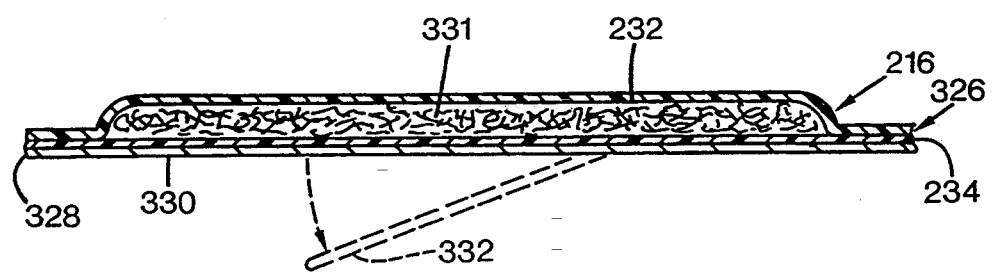
FIG. 17 is a partial sectional view of the pad of FIG. 16, taken along line 17—17 of FIG. 16.
Figure 18:
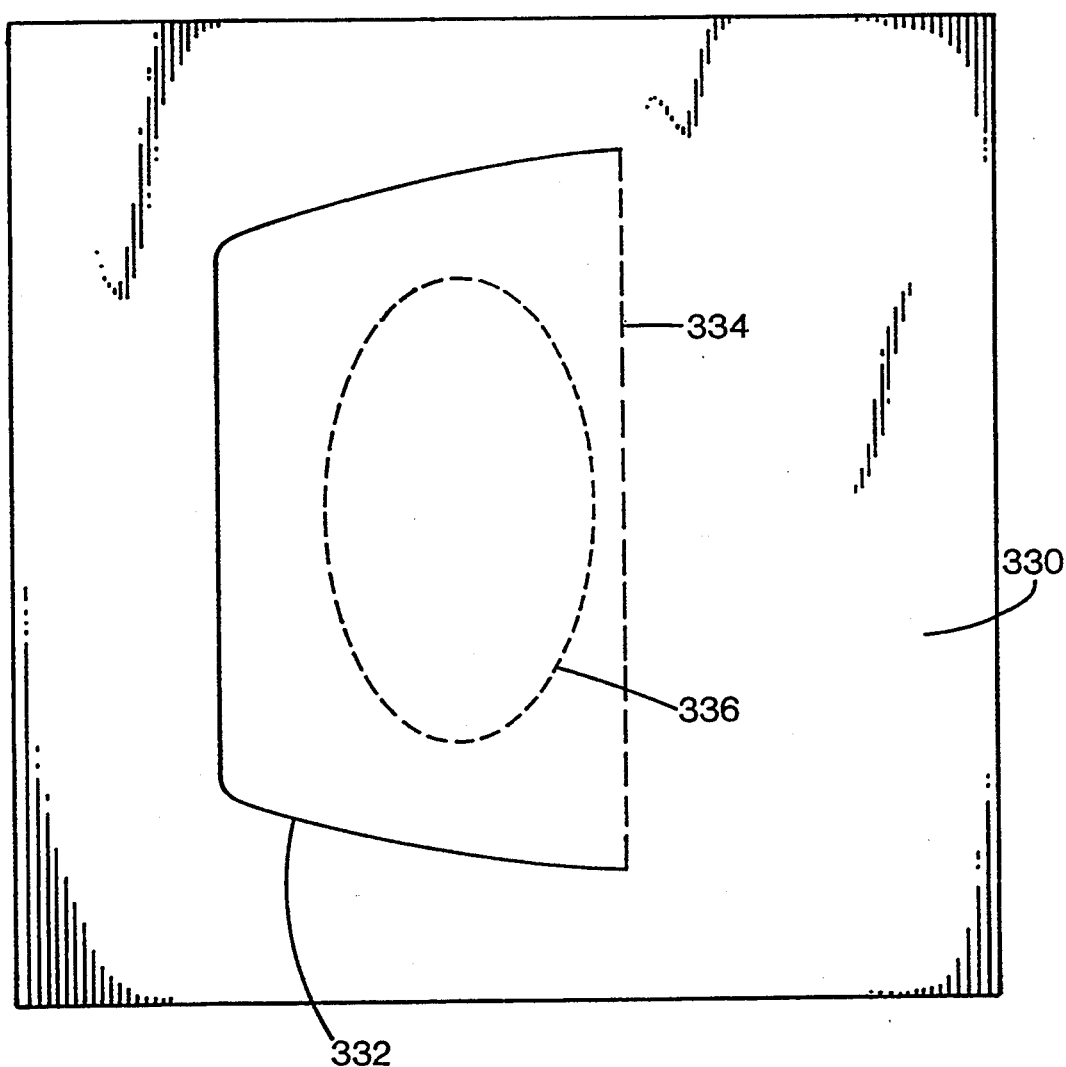
FIG. 18 is a bottom view of the embodiment shown in FIG. 16.

With reference to FIGS. 16–18, the absorbent pad 216 may be secured by conventional means to the upper surface of a support 326.

The support 326 typically is of a material providing a barrier to the passage of a liquid through the support. For example, the support 326 may include a liquid impermeable backing sheet 324, such as of polyethylene. The backing sheet may comprise one surface of the pad 216 with the other pad surface 232 being of a liquid permeable material, as previously described. The sheets 232 and 234 also enclose fibers 331 to which antimicrobial particles are adhered. The pad 216 is mounted to a backing material or base 328. In the illustrated form, the base 328 is formed of a wood pulp paper sheet such as a 250 to 280 pound per ream bleached paperboard.

The paper sheet or other base material imparts stiffness to the support, making it easier for the user to wipe the absorbent pad 216 across the spill. To minimize the possibility the user directly contacting a spill, a handle 332 may be provided on the bottom side 330 of base 328. Handle 332 may be affixed to bottom side 330 by any known means. However, when bottom side 330 is formed of a paper sheet, the sheet may be perforated, as best seen in FIG. 18. The perforations 334 and 336 define the handle 332. The self-contained fold-open handle 332 defined by perforations 334 and 336, when closed, allows for easy storage of the wipes, as they may be readily stacked. By simply tearing the perforations 334 and 336 and folding the handle 332 away from bottom side 330 of the base (see the dashed lines in FIG. 17), the user forms the handle 332 for grasping during clean up of the spill.

Figure 19:
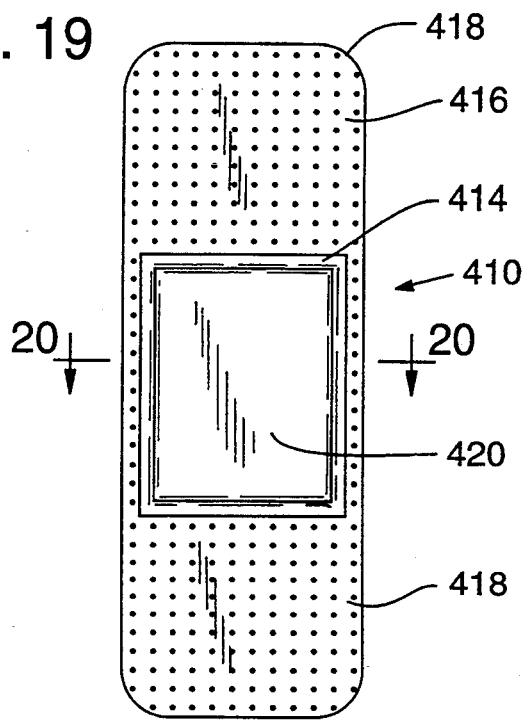
FIG. 19 illustrates a plan view of a bandage incorporating fibers of the present invention.
Figure 20:
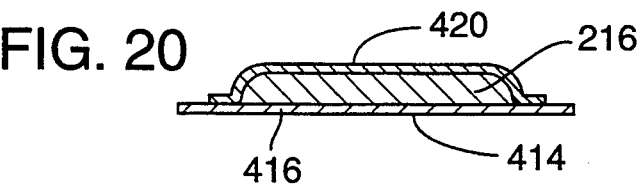
FIG. 20 is a sectional view of the bandage of FIG. 19, taken along line 20—20 of FIG. 19.

With reference to FIGS. 19–22, absorbent structures in the form of bandages or dressings are shown. In FIGS. 19 and 20, a bandage 410 for application to a wound to absorb blood and other bodily fluids is shown. An absorbent pad 216 (FIG. 20) is securely mounted to an exterior or pad mounting surface 414 of a backing strip 416. Any suitable mounting or securing means may be used to affix pad 216 to the surface 414 of the strip 416. However, it is preferable for surface 414 to be coated with an adhesive so that the pad 216 may be adhesively mounted in place. An exemplary adhesive is ethylene vinyl acetate adhesive. It is also desirable for the overall surface 418 of backing strip 416 to be coated with a conventional adhesive. Surface 418 is the surface which is affixed to the area of the skin surrounding the wound. Conventional "peel-back" tabs may be used to protect the adhesive coating and pad 216 until the bandage is to be applied. This type of backing strip is well known in the art.

The backing strip 416 may be of any known flexible material suitable for application to the skin. It is preferable for the strip 416 to be of a material which is impermeable to the passage of liquid so that fluid from a wound is contained by the bandage. However, the strip 416 may be apertured or otherwise breathable to permit air to reach the wound to promote the healing process. A specific example of a suitable backing strip 416 is a polyethylene film.

As in the other structures described, a variy of combinations of antimicrobials and other particles may be used in such a bandage. Two different particles, such as antimicrobials in particulate form, may be adhered to the same fiber. In the alternative, each different type of antimicrobial particle or other particle may be adhered separately to different fibers. Also, blends of fibers may be included in absorbent structures such as pad 216. For example, these blends may include fibers with adhered antimicrobial (one or more antimicrobials) particles and adhered super-absorbent particles; fibers with one or more antimicrobial particles without super-absorbent particles blended with fibers having adhered super-absorbent particles with or without antimicrobial particles; and combinations of such fibers with untreated fibers and/or binder coated fibers without super-absorbent particles or antimicrobial particles. In addition, other particles, such as anticoagulants may be attached to the fibers.

The absorbent pad 216 of bandage 410 may also include a cover sheet 420. Cover sheet 420 is typically made of any suitable material which will readily permit the passage of liquid through the cover sheet to the absorbent pad 216, such as nonwoven fiber webs of fibers such as, for example, rayon, nylon, polyester, propylene and blends thereof. One specifically preferred cover sheet material is a 70 percent rayon/30 percent polyester blend having a basis weight of 18 g/m² from Scott Paper Company.

It is preferable to have the cover sheet 420 of a heat bondable material. When the fibers of the absorbent structure 216 are heated in a thermobonder during the manufacturing process, the heat bondable cover sheet will likewise be heat bonded to the fibers as the fibers themselves are heat bonded. Alternatively, the cover sheet 420 may be adhesively bonded to the absorbent pad 216 or unbonded.

Figure 21:
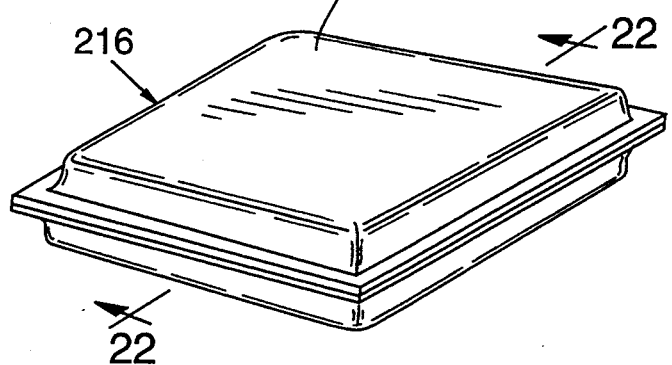
FIG. 21 is a perspective view of an absorbent structure of fibers of the present invention.
Figure 22:
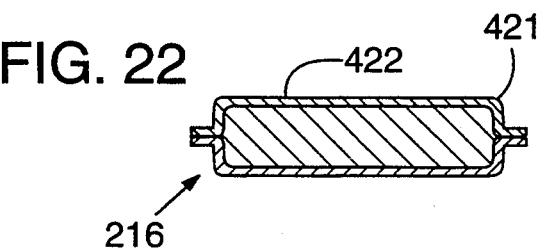
FIG. 22 is a cross-sectional view of the structure of FIG. 21, taken along line 22—22 of FIG. 21.

The dressing 216 shown in FIGS. 21 and 22 illustrates unbonded fibers 421 placed within an enclosure 422. Enclosure 422 has at least one liquid permeable surface through which fluid or liquid may pass to be absorbed by the fibers. The enclosure containing the loose fibers may be secured to the skin using adhesive tape, for example. A bonded fiber core 421 is most preferred as it adds to the strength and integrity of the dressing or bandage. Again, the fibers 421 preferably include antimicrobial particles attached to at least some of the fibers.

Figure 23:
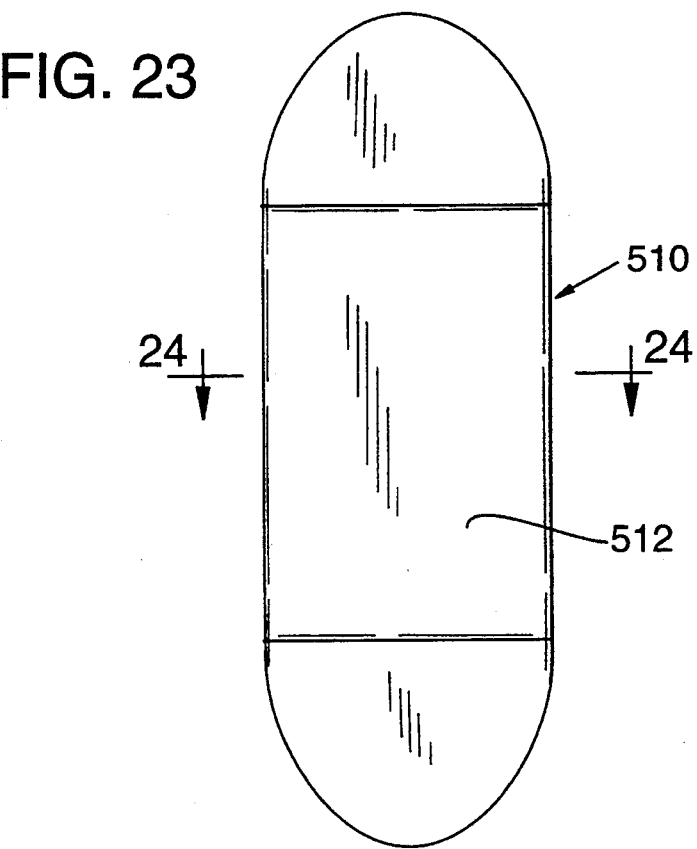
FIG. 23 is a plan view of a feminine hygiene appliance incorporating fibers of the present invention.
Figure 24:
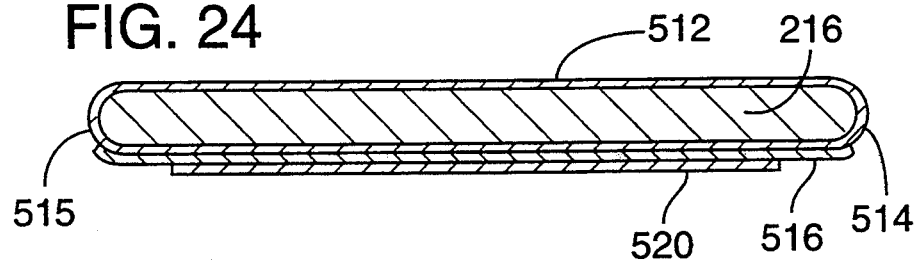
FIG. 24 is a sectional view of the appliance of FIG. 23 taken along line 24—24 of FIG. 23.

FIGS. 23 and 24 illustrate fibers of the present invention incorporated into a feminine hygiene appliance such as a feminine pad or tampon. In this case, the feminine pad 510 is illustrated as having a cover sheet 512. The loose fibers having adhered antimicrobial particles, which may alternately be in the form of a bonded pad, are included within the interior of the feminine appliance as indicated at 216 in FIG. 24. The cover 512 is preferably liquid permeable so that bodily fluids may reach the interior of the pad for purposes of absorption. The cover 512 may be wrapped around the core 216 (as indicated by edges 514, 515). A backing sheet 516, preferably of a liquid impermeable material, may be adhered to the edges 514, 515 at the underside of the core. An adhesive containing strip, such as indicated at 520, which may have a peelable or removable cover, may be mounted to the backing sheet 516 for use in adhering the pad, for example a user's undergarment, during use.

Figure 25:
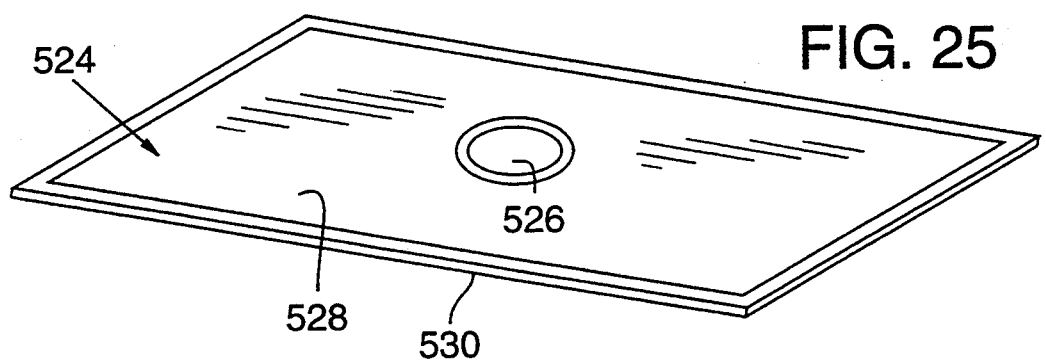
FIG. 25 is a perspective view of a surgical drape manufactured from fabric of fibers of the present invention.
Figure 26:
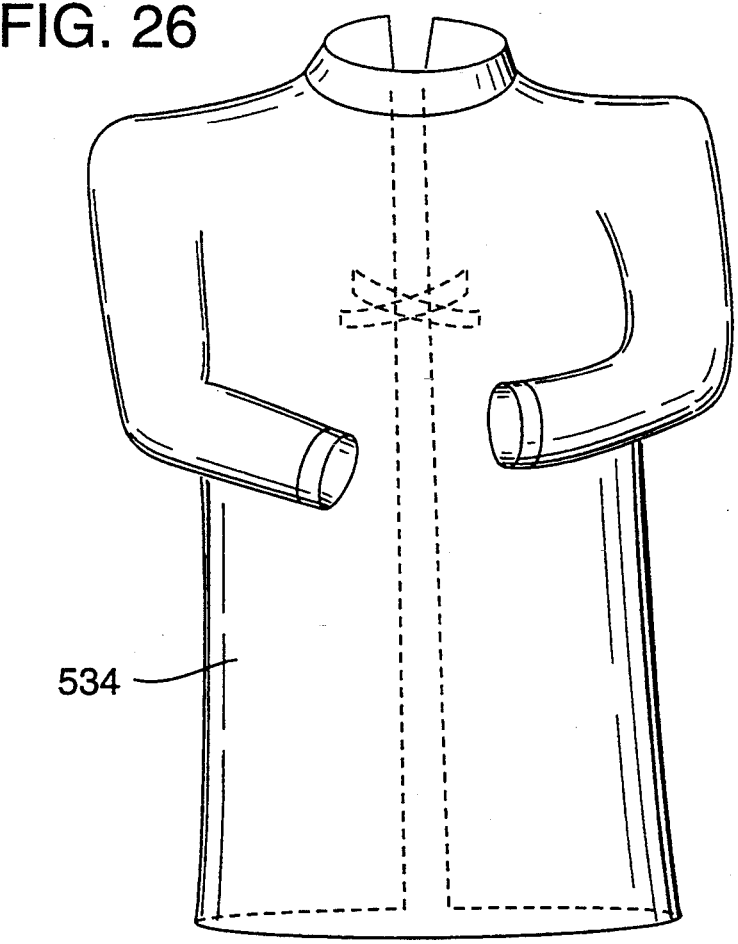
FIG. 26 is a perspective view of a garment, in this case a surgical gown, manufactured from fabric of fibers of the present invention.
Figure 27:
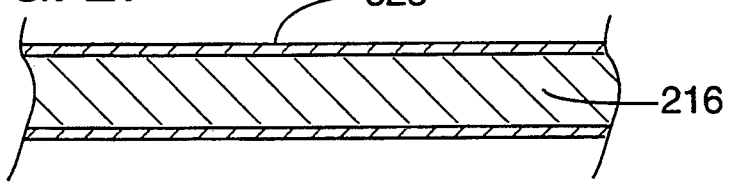
FIG. 27 is a sectional view or a portion of the fabric of the drape of FIG. 25.

FIGS. 25-27 represent respectively, fibers of the present invention, with adhered particles such as antimicrobial particles, formed into surgical drapes and surgical gowns. Again, other particles, such as super-absorbent particles may also be adhered to the fibers by the binder material. As shown in FIG. 27, the fabric sheet used in these absorbent structures may include a cover sheet 528 and a backing sheet 530 with fibers 216 therebetween, and thus comprising a core between the cover and backing sheets. Typically, the cover sheet 528 is made of any suitable material which will readily permit the passage of liquid through the cover sheet to the fibers 216. The cover sheet may be of materials such as previously described. Also, the backing sheet 530 may be made of a liquid impermeable material such as previously described, with 0.004 inch polyethylene film being one preferred example. The cover sheet 216 and backing sheet 218 may be adhesively bonded at the periphery of the fabric, and around any openings, such as opening 526 providing access to a surgical area, included therein. The core 216 may also be bonded. Also, the backing and covering sheets may be of a heat bondable material and may be adhered to one another and to the core by heat bonding.

It should also be understood that fibers of the invention with and without adhered particles, may be simply formed in bonded or loose mats as well as in other structures (including rigid structures and nonabsorbent structures) apart from the specific examples mentioned above in connection with FIGS. 6-27. Also, one or more types of particulate materials may be included in a given structure.

EXAMPLE 15

This example describes the attachment of an odor absorbing zeolite material to fibers, such as wood pulp fibers. These fibers may be included in odor absorbing structures, such as adult incontinent products, diapers, feminine appliances and shoe inserts. Fibers with adhered odor absorbing zeolite materials are useful in any other application where odors are troublesome.

One specific zeolite used in this example is a molecular sieve, available from UOP of Tarrytown, N.Y. under the trademark SMELLRITE/ABSCENTS. This particular molecular sieve has organophilic micropores which attract odor molecules and trap them within its porous structure to effectively remove them from the environment. The median particle size of these microsieves is 3.5 to 6.5 microns. These particles are thermally stable to over 800° C. and over a pH range of from 3 to 10.

In accordance with this specific example, one hundred seven grams of Southern bleached kraft (NB316, 7% moisture) were placed in a recirculating duct including a fan or blower. The fan was turned on and the fluff became air entrained. A mixture (45% solids) of seventy-five grams of deionized water and twenty-four grams of Reichhold Chemicals' (Inc., Dover, Del.) 97-910 binder were sprayed onto the fluff through a port in the duct. After the latex was sprayed, the loop was turned off and 10 grams of a sodium aluminosilicate zeolite (ABSCENTS TM particles) was added. The fan was then restarted and the mixture circulated for one minute to ensure complete mixing. This yielded a mixture that was approximately 10% binder, 10% zeolite, and 80% fiber. the mixture was shunted into an air permeable nylon bag, collected and placed in a plastic bag. A sample of the still damp material was then taken, formed into a pad on a laboratory pad former and submitted to analytical services for a gravimetric determination of the amount of zeolites attached to the fiber. On ashing at 925° C., 75% of the added zeolite was rained in the sample. Three 10.2 gram samples of this material were formed into airlaid pads, thermobonded at 140° C. for 30 seconds and sealed in a plastic bag. Also, three 1.2 gram samples of the fluff were wetlaid into six inch hand sheets, air dried overnight, and sealed in a plastic bag. The airlaid pads and hand sheets were also ashed to determine the amount of added zeolite retained in the sample during these processes. These tests revealed the loss of some zeolites during the airlaying and wetlaying processes. However, when tested for the odor absorbing efficiency, using gas chromatography testing as explained in an article entitled "Smellrite/Abscents a Unique Additive for Odor Control," by Bonnie Marcus, in TAPPI Proceedings, Nonwovens Conference, pages 283-285 (1990), the attached zeolites remained 75% to 95% efficient in absorbing odors in comparison to zeolites which were not attached to fibers.

In further testing, by diluting the binder by adding deionized water (to an 11.3% solids level) 93% of the zeolites added to the fibers were rained on the fibers during airlaying of the zeolite containing fibers into a pad.

Therefore, binder coated fibers with attached zeolites are an effective means for retaining zeolites in an absorbent structure while still substantially retaining the odor absorbing properties of the zeolite particles. In addition, fibers with substantially continuous binder coatings can be produced and used in adhering the particles in place.

EXAMPLE 16

In this example, microsponges, such as 5 to 300 micron diameter microsponges from Advanced Polymer Systems, Inc. of Redwood City, Calif., can be attached to a binder containing fibers such as explained above in connection with Examples 14 and 15 (to name a few). These microsponges may be saturated with an antimicrobial material for use in manufacturing antimicrobial structures such as previously explained. These microsponges may also incorporate medicines and active agents for skin care as well as cosmetics. When incorporated into an absorbent structure, such as a pad, the active agents in the microsponges would be available to perform their function during use of the pad or other structure. Perfumes and fragrances may similarly be included in the microsponges.

EXAMPLE 17

In addition to odor absorbing zeolites, for example aluminosilicates that excel in absorption and ion exchange are available in both natural and synthetic forms. These zeolites are widely used as industrial catalysts, drying agents and for certain compounding applications. These materials may be attached to fibers as explained above in connection with Examples 15 and 16.

Also, Kanebo Ltd., of Japan, has added a germicidal ion to zeolites and developed a particulate antibacterial agent known as BACTEKILLER antibacterial agent. This material has been incorporated into polyester and nylon fibers. However, when these materials are incorporated into the fibers, the effective surface area of the materials is reduced due to the encapsulation in whole or in part of these zeolites in the fibers. By attaching zeolites to the surface of binder coated fibers as previously explained, the efficiencies of these particles in performing their functionality, for example as a germicide, would be substantially improved.

Zeolites modified by copper, silver or zinc ions have also exhibited excellent antibacterial and antifungicidal properties and can similarly be attached to fibers as previously described. Again, fibers with attached zeolite particles, with or without additional particles, may be used or blended with other fibers in various structures.

Having illustrated and described the principles of our invention with reference to several preferred embodiments and examples, it should be apparent to those of ordinary skill in the art that such embodiments of our invention may be modified in detail without departing from such principles. We claim as our invention all such modifications as come within the true spirit and scope of the following claims.

I claim:

1. A fiber product which comprises dry discontinuous fibers having a starch binder on at least a portion of the fiber surfaces, at least seventy percent of the starch binder coated fibers being unbonded to one another, solid particles being adhered to the fibers by the binder without the binder entirely coating the particles.

2. A fiber product according to claim 1 in which the solid particles comprise superabsorbent particles which can absorb in excess of ten parts ok liquid per part particle.

3. A fiber product according to claim 1 in which at least about ninety-five percent of the starch binder coated fibers are unbonded to one another.

4. An absorbent structure comprised of fibers of claim 1.

5. A fiber product according to claim 1 which is comprised of fibers of claim 1 air laid into a mat.

6. A fiber product which comprises discontinuous fibers having a starch binder on at least a portion of the fiber surfaces, superabsorbent solid particles which can absorb in excess of ten parts liquid per part particle and which are adhered to the fibers by the binder, and the superabsorbent solid particles not being entirely coated by the binder.

7. A fiber product according to claim 6 which is comprised of fibers of claim 6 air laid into a mat.

* * * * *